United States Patent
Lee et al.

(10) Patent No.: US 12,359,188 B2
(45) Date of Patent: *Jul. 15, 2025

(54) METHOD FOR PRODUCING THERAPEUTIC EXOSOMES FROM NANOELECTROPORATION AND OTHER NON-ENDOCYTIC CELL TRANSFECTION

(71) Applicant: Ohio State Innovation Foundation, Columbus, OH (US)

(72) Inventors: Ly James Lee, Columbus, OH (US); Junfeng Shi, Dublin, OH (US); Zhaogang Yang, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,442

(22) Filed: May 19, 2023

(65) Prior Publication Data

US 2023/0313170 A1  Oct. 5, 2023

Related U.S. Application Data

(63) Continuation of application No. 16/635,471, filed as application No. PCT/US2018/045333 on Aug. 6, 2018, now Pat. No. 11,674,130.

(60) Provisional application No. 62/541,157, filed on Aug. 4, 2017.

(51) Int. Cl.
| | |
|---|---|
| C12N 13/00 | (2006.01) |
| C12M 1/42 | (2006.01) |
| C12M 3/06 | (2006.01) |
| C12N 15/87 | (2006.01) |

(52) U.S. Cl.
CPC ............. *C12N 13/00* (2013.01); *C12M 23/16* (2013.01); *C12M 35/02* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 7,338,796 B1 | 3/2008 | Davalos et al. | |
| 8,524,679 B2 * | 9/2013 | Pachuk | A61P 1/16 536/24.5 |
| 2004/0197314 A1 * | 10/2004 | Delcayre | C07K 14/47 424/93.21 |
| 2014/0256047 A1 | 9/2014 | Lee et al. | |

FOREIGN PATENT DOCUMENTS

| | | |
|---|---|---|
| CN | 102596177 A | 7/2012 |
| WO | 2017054086 A1 | 4/2017 |

OTHER PUBLICATIONS

Chang, L. et al. 2016. First published Jul. 9, 2015. 3D nanochannel electroporation for high-throughput cell transfection with high uniformity and dosage control. Nanoscale 8: 243-252; specif. pp. (Year: 2016).*
Chang, L. et al., 3D Nanochannel Electroporation for High-Throughput Cell Transfection with High Uniformity and Dosage Control, Nanoscale, 2016, vol. 8, pp. 243-252.
Chang, L. et al., 3D Nanochannel Electroporation for High-Throughput Cell Transfection with High Uniformity and Dosage Control, 2016, Figures 1-3.
Mizrak, A. et al., Genetically Engineered Microvesicles Carrying Suicide mRNA/Protein Inhibit Schwannoma Tumor Growth, The American Society of Gene & Cell Therapy, Molecular Therapy, Jan. 2013, pp. 101-108, vol. 21, No. 1.
Pegtel, D.M. et al., Functional delivery of viral miRNAs via exosomes, The Proceedings of the National Academy of Sciences, Apr. 6, 2010, pp. 6328-6333, vol. 107, No. 14.
Shi, J., Development of Nanoelectroporation-based Biochips for Living Cell Interrogation and Extracellular Vesicle Engineering, Dissertation, 2017, pp. 130-136.
Kanuma, T. et al., CD63-Mediated Antigen Delivery into Extracellular Vesicles via DNA Vaccination Results in Robust CD8+ T Cell Responses, The Journal of Immunology, May 15, 2017, pp. 1-13, 198.
McKnight, T.E. et al., Tracking Gene Expression after DNA Delivery Using Spatially Indexed Nanofiber Arrays, American Chemical Society, Nano Letters, 2004, pp. 1213-1219, vol. 4, No. 7.
Lamichhane, T.N. et al., Exogenous DNA Loading into Extracellular Vesicles via Electroporation is Size-Dependent and Enables Limited Gene Delivery, American Chemical Society, Molecular Pharmaceutics, 2015, pp. 3650-3657, 12.
Obregon, C. et al., Exovesicles from Human Activated Dendritic Cells Fuse with Resting Dendritic Cells, Allowing Them to Present Alloantigens, American Journal of Pathology, Dec. 2006, pp. 2127-2136, vol. 169, No. 6.
Raposo, G. et al., Extracellular vesicles: Exosomes, microvesicles, and friends, Journal of Cell Biology, 2013, pp. 373-383, vol. 200, No. 4.
Tabar, M.S. et al., Evaluating Electroporation and Lipofectamine Approaches for Transient and Stable Transgene Expressions in Human Fibroblasts and Embryonic Stem Cells, 2015, Cell Journal, pp. 438-450, vol. 17, No. 3.

(Continued)

*Primary Examiner* — Adam Weidner
*Assistant Examiner* — Sharon M. Papciak
(74) *Attorney, Agent, or Firm* — Standley Law Group LLP; Jeffrey S. Standley; Kenny W. Pung

(57) ABSTRACT

Therapeutic extracellular vesicles (EVs) containing high copies of functional nucleic acids and other biomolecules are produced in large quantities by laying donor cells on a surface of a chip, adding various plasmids, other transfection vectors and their combinations to a buffer on the chip, applying a pulsatic electric field across the cells laid on top of the chip surface and plasmids/vectors buffer solution below the chip surface, and collecting the EVs secreted by the transfected cells. The chip surface has a three-dimensional (3D) nanochannel electroporation (NEP) biochip formed on it, capable of handling large quantities of the donor cells. The buffer is adapted for receiving plasmids and other transfection vectors.

25 Claims, 19 Drawing Sheets

(56) References Cited

OTHER PUBLICATIONS

Byk-Chemie GMBH, BYKJET-9150, High molecular weight wetting and dispersing additive for solvent-free UV-curable inkjet inks. Suitable for all pigment types., Data Sheet, Issue Oct. 2014, 2 pages.
CFC, Chinese Oncology Clinical Yearbook 2015, China Cancer Foundation et al., Sep. 2016, pp. 36-37.

* cited by examiner

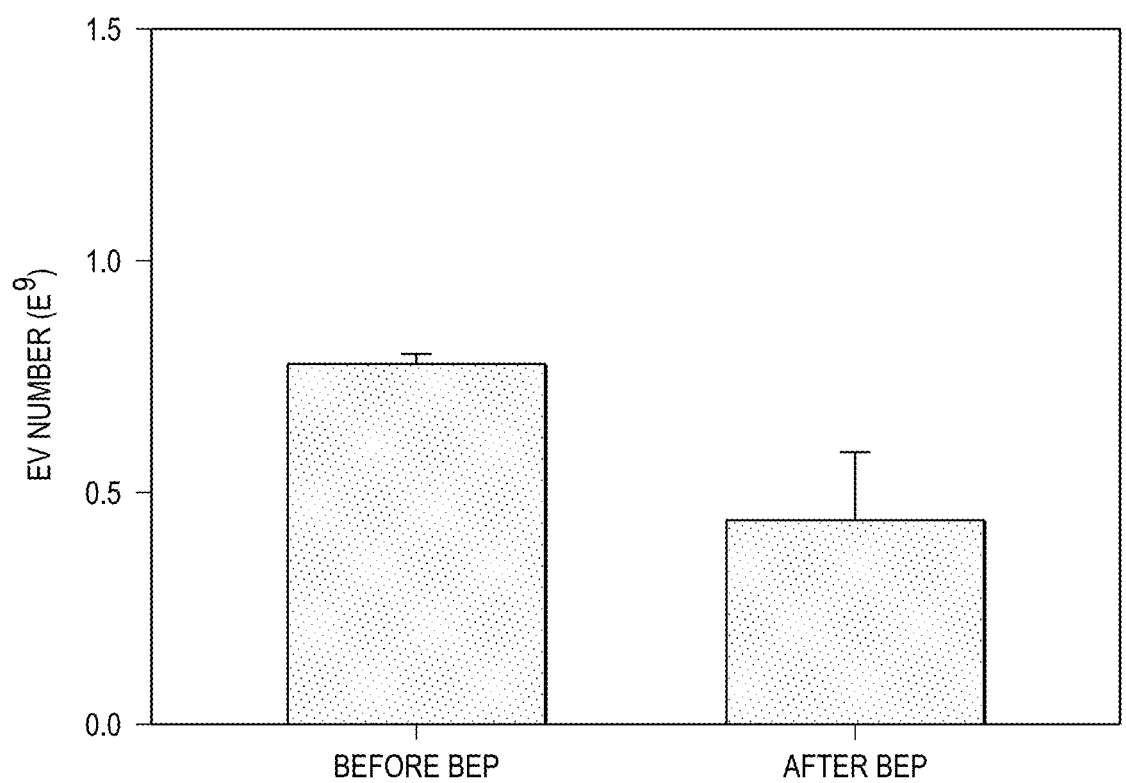

METHOD FOR PRODUCING THERAPEUTIC EXOSOMES FROM NANOELECTROPORATION AND OTHER NON-ENDOCYTIC CELL TRANSFECTION

CROSS-REFERENCE TO RELATED APPLICATIONS

This application is a continuation of U.S. application Ser. No. 16/635,471 filed on Jan. 30, 2020, now U.S. Pat. No. 11,674,130 issued on Jun. 13, 2023, which is a national stage of International Patent Application No. PCT/US2018/045333 filed on Aug. 6, 2018, which claims priority to U.S. Provisional Patent Application No. 62/541,157 filed on Aug. 4, 2017, the disclosures of which are hereby incorporated by reference as if fully restated herein.

TECHNICAL FIELD

The present invention relates to methods for producing therapeutic extracellular vesicles (EVs), exosomes in particular, that contain functional messenger RNAs (mRNAs), microRNAs (miRs), short hairpin RNAs (shRNAs), proteins, and other biomolecules by non-endocytic delivery of DNA plasmids and other vectors into donor cells in a way that the strong stimulation caused by delivery triggers donor cells to generate a large number of vesicles within the cell while the non-endocytic delivery of DNA plasmids/vectors leads to fast transcription of RNAs and translation of proteins within cytoplasm, allowing those functional biomolecules to be encapsulated in the vesicles endogenously before they are secreted out from donor cells as EVs.

BACKGROUND

Extracellular vesicles (EVs), including exosomes, microvesicles and other vesicles, are secreted by numerous cell types. In the human body, there are >10E12 EVs in 1 mL blood and they also exist in various body fluids. Exosomes are nano-vesicles (40-150 nm), while microvesicles have sizes varied from <100 nm to >1 micron. They contain both coding and non-coding RNAs and their fragments, DNA fragments, proteins, and other cell related biomolecules. EVs and their biomolecule contents have been proposed as biomarkers for disease diagnosis. In addition, they play major roles in cell-cell communications in tumor microenvironment and circulation.

EVs loaded with functional RNAs and proteins have also been suggested as drugs and drug carriers for therapeutic applications. To deliver specific nucleic acids and/or proteins to target tissues or cell types in vitro and in vivo requires methods that can produce EVs with either endogenous or exogenous therapeutic cargos.

Post-insertion of exogenous small interference RNA (siRNA) and shRNA plasmids into pre-existed exosomes by conventional bulk electroporation (BEP) has been developed in recent years. Although their therapeutic functions have been successfully demonstrated in several mouse models for cancer and non-cancer diseases, this approach faces many limitations. First, post-insertion of large biomolecules such as DNA plasmids, mRNAs, and proteins into nano-sized exosomes is inefficient. Secondly, the strong electric field generated by BEP would break up many exosomes leading to a low yield of therapeutic exosomes. Furthermore, many large biomolecules such as mRNAs and proteins are difficult and expensive to be synthesized exogenously.

It would be highly desirable if new methods can be developed, that may transfect donor cells with DNA plasmids or other vectors to produce a large number of exosomes or other EVs containing therapeutic RNA and protein targets endogenously.

In a prior U.S. patent application Ser. No. 14/282,630, we developed a nanochannel electroporation (NEP) biochip that can deliver DNA plasmids or other charged particulates and molecules into individual cells non-endocytically with good dosage control. Herein, we demonstrate that NEP can produce a large number of therapeutic exosomes containing high copies of functional mRNA and microRNA targets, not achievable by the aforementioned post-insertion methods. In addition to NEP, other non-endocytic delivery methods such as gene gun, micro/nano-injection, etc. may also achieve a similar performance if they can provide proper cell stimulation and fast plasmid/vector delivery.

SUMMARY

The present invention is related to the development of new concept and methods that DNA plasmids and other vectors can be non-endocytically delivered into donor cells with strong cellular stimulation such that a large number of vesicles and transcribed RNAs as well as translated proteins are formed within the transfected cells. Cells would secret many extracellular vesicles (EVs) containing specific RNA and protein targets with therapeutic functions.

To demonstrate the aforementioned design concept, a three-dimensional (3D) NEP biochip is fabricated, that can transfect many donor cells with pre-specified DNA plasmids to secret 10~100 folds more EVs, including exosomes, containing high copies of intact mRNA and miR targets up to many thousands folds more than those in EVs secreted from the non-transfected donor cells.

Some aspects of the invention are achieved by a method of producing a large number of therapeutic extracellular vesicles (EVs) containing high copies of functional nucleic acids and other biomolecules. Such a method comprises the steps of:
- laying donor cells on a surface of a chip, the surface having a three dimensional (3D) nanochannel electroporation (NEP) biochip formed thereon;
- adding various plasmids, other transfection vectors and their combinations to a buffer on the chip;
- applying a pulsulatic electric field across the cells laid on top of the chip surface and plasmids/vectors buffer solution below the chip surface, resulting in strongly stimulating the cells and delivering plasmids/vectors into cells non-endocytically; and
- collecting EVs secreted by the transfected cells.

In some of these methods, the diameter of nanochannels is between 50-900 nm.

In some of these methods, wherein the plasmids and vectors transcribe mRNA, microRNA, shRNA, and other RNAs, and lead to translation of proteins and other biomolecules in the transfected cells.

In some embodiments of the method, the EVs secreted by the transfected cells contain the transcribed mRNA, microRNA, shRNA, and other RNAs, and the translated proteins and other biomolecules.

In some of the embodiments of the method, wherein means to increase the expression of heat shock proteins and other proteins that can promote vesicle formation and exocytosis in the transfected cells are added to the system, wherein the means includes a thermal shock treatment of the cells, or addition of heat shock proteins in cell culture.

In some of the embodiments, means to increase the expression of proteins that promote exosome formation in the transfected cells are added to the system, wherein the means includes co-transfection of CD63, CD9 and other DNA plasmid.

In some embodiments, multiple DNA plasmids and other vectors are delivered to the transfected cells sequentially to promote co-localization of RNA/protein targets and EV secretion.

In some embodiments, exogenous biomolecules such as DNA plasmids, other transfection vectors, RNAs, proteins/peptides, small molecule drugs are encapsulated within vesicles in cells and secreted out as therapeutic EVs by sequential transfection of donor cells by NEP. In some of these cases, in addition to NEP, other cell transfection methods that provide strong stimulation to donor cells to facilite EV secrection and non-endocytic plasmid/vector delivery for fast RNA transcription and protein translation are used to produce therapeutic EVs with similar efficacy. In further of these cases, the other cell transfection methods include, gene gun, and micro- or nanoinjection.

In some of the embodiments, the plasmids and/or other vectors are tethered on nano- or micron-sized gold or other solid particles, and those particles are injected into donor cells under a pneumatic force using a gene gun to cause strong cell stimulation and non-endocytic plasmis/vector delivery.

In some of the embodiments, the plasmids and/or other vectors are tethered on a nano- or micron-sized tip array, and donor cells are pultruded by those tips to cause strong cell stimulation and non-endocytic plasmis/vector delivery into donor cells.

Other aspects of the invention are achieved by a device for producing a large number of therapeutic extracellular vesicles (EVs) containing high copies of functional nucleic acids and other biomolecules, comprising: a chip having a three-dimensional (3D) nanochannel electroporation (NEP) biochip and a buffer for receiving formed thereon, the buffer adapted for receiving plasmids and other transfection vectors.

Other aspects of the invention comprises cells transfected by any of the foregoing methods.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. In the drawings:

FIGS. 16A to 16E compare secreted EVs containing miR-128 by NEP transfection of DNA plasmid to MEF cells vs. existing EVs loaded with pre-collected miR-128 by BEP post-insertion;

DETAILED DESCRIPTION

Figure 1:
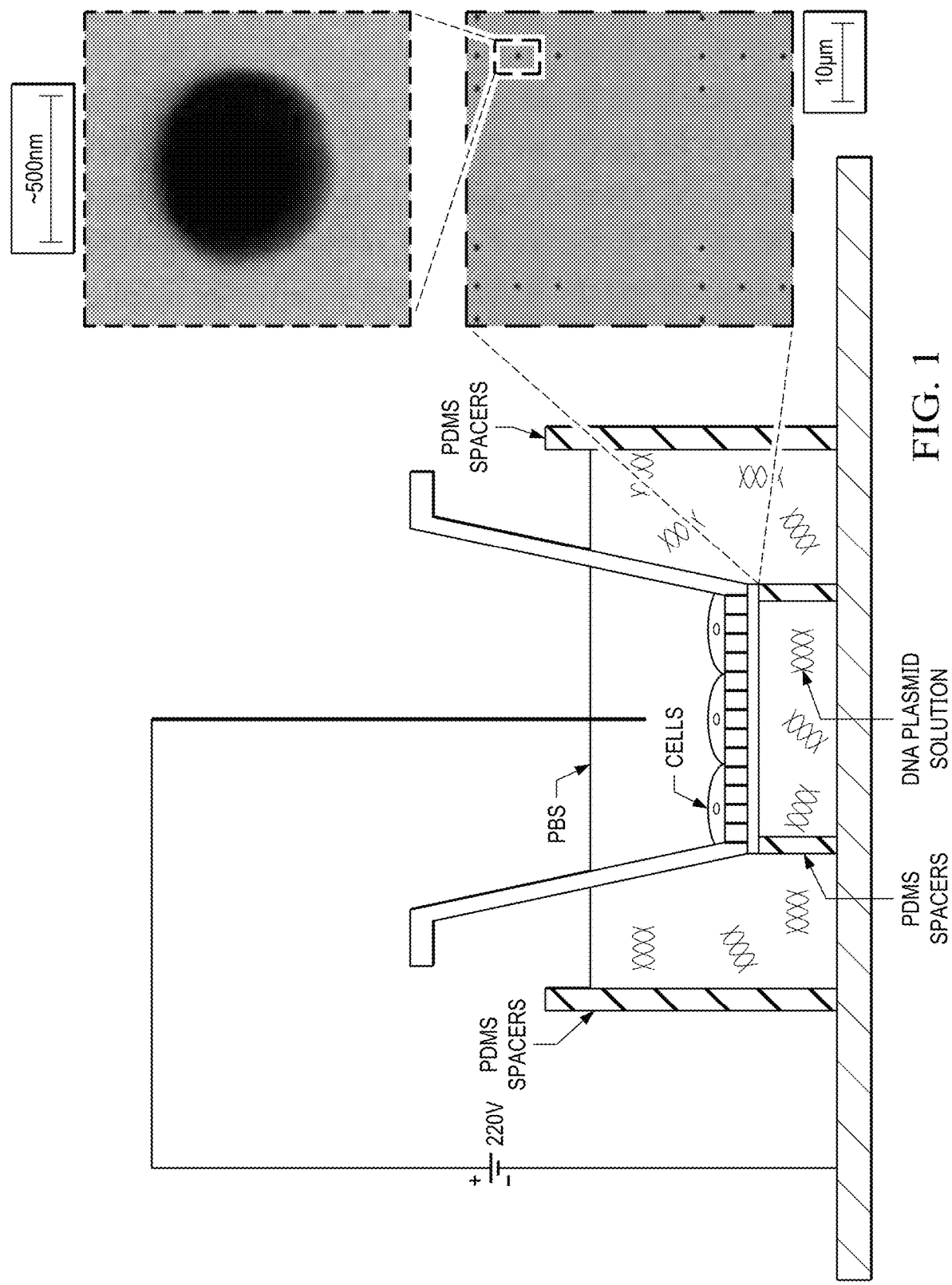
FIG. 1 is a schematic of a 3D Nanochannel Electroporation (NEP) biochip for donor cell transfection.

Example 1-3D NEP Biochip Schematic and Comparison of EV Secretion and EV mRNA Content Using Different Transfection Methods FIG. 1 shows the schematic of a 3D NEP biochip with a single layer of donor cells laid on the chip surface. After overnight cell incubation, the DNA plasmids pre-loaded in PBS buffer were injected into individual donor cells via nanochannels using a 220 volts electric field across the nanochannels. Various electroporation conditions such as voltage level, pulse number and pulse length can be chosen.

Figure 2A:
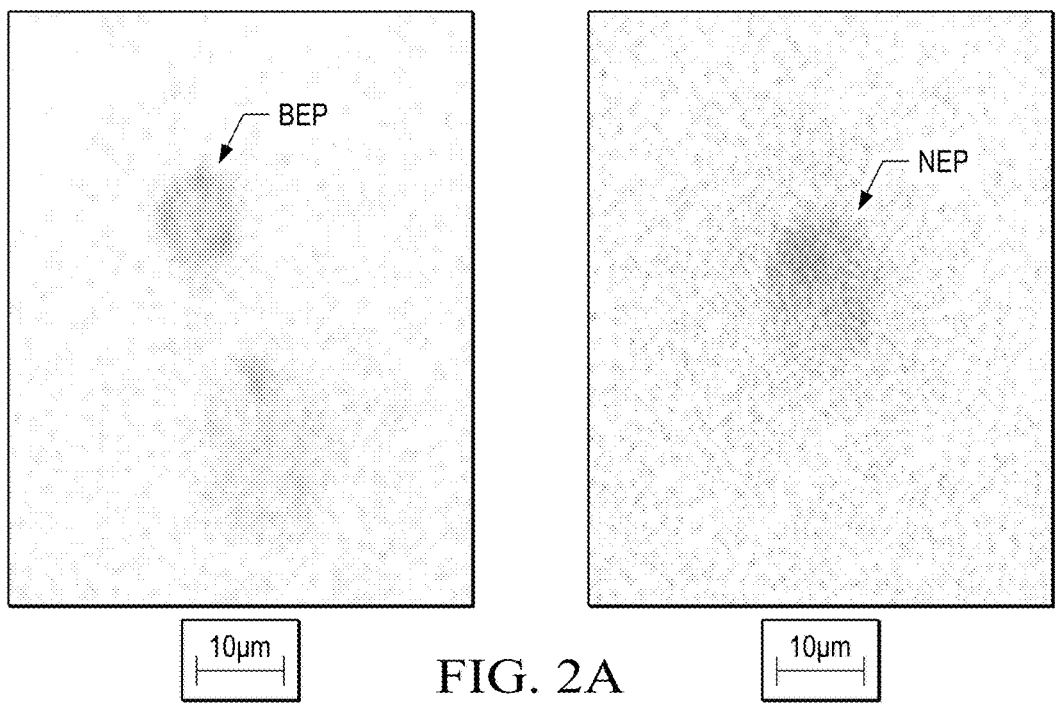
FIG. 2A shows a comparison of cell images of BEP and NEP based cell transfection at 1 hr post-transfection using Yoyo-1 fluorescence labelled Achaete-Scute Complex Like-1 (Ascl1) DNA plasmid, a neuronal related gene.
Figure 2B:
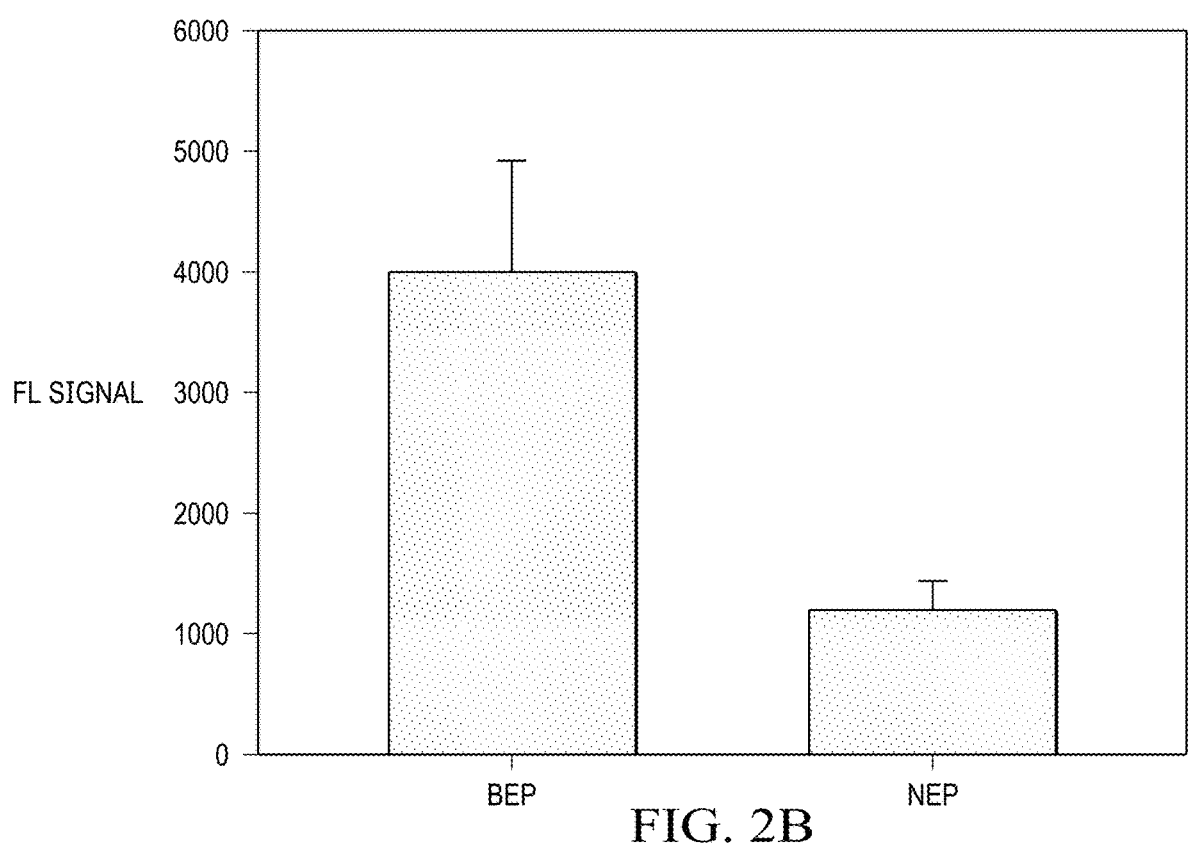
FIG. 2B shows a graphical comparison of the fluorescence intensity in the images of FIG. 2A.

Using Yoyo-1 fluorescence dye labelled Achaete-Scute Complex Like-1 (Ascl1) DNA plasmid, FIGS. 2A and 2B show transfected cells imaged using fluorescence microscopy 1 h after transfection by either BEP or NEP under a wavelength of 488 nm. The fluorescence intensity was calculated by NIS software. Comparison of fluorescence intensity in these two groups is given as bar charts. The results show that BEP at the manufacturer recommended best conditions could deliver nearly 3 folds more plasmids than NEP at 220 volts with five 10-ms pulses to the MEF cells. However, most plasmids were still near the cell surface 1 h after BEP transfection, while the injected plasmids by NEP have already been uniformly diffused within cytoplasm at the same time. This implies that BEP based cell transfection relies mainly on electroporation-mediated endocytosis, while NEP based cell transfection is non-endocytic.

Figure 3:
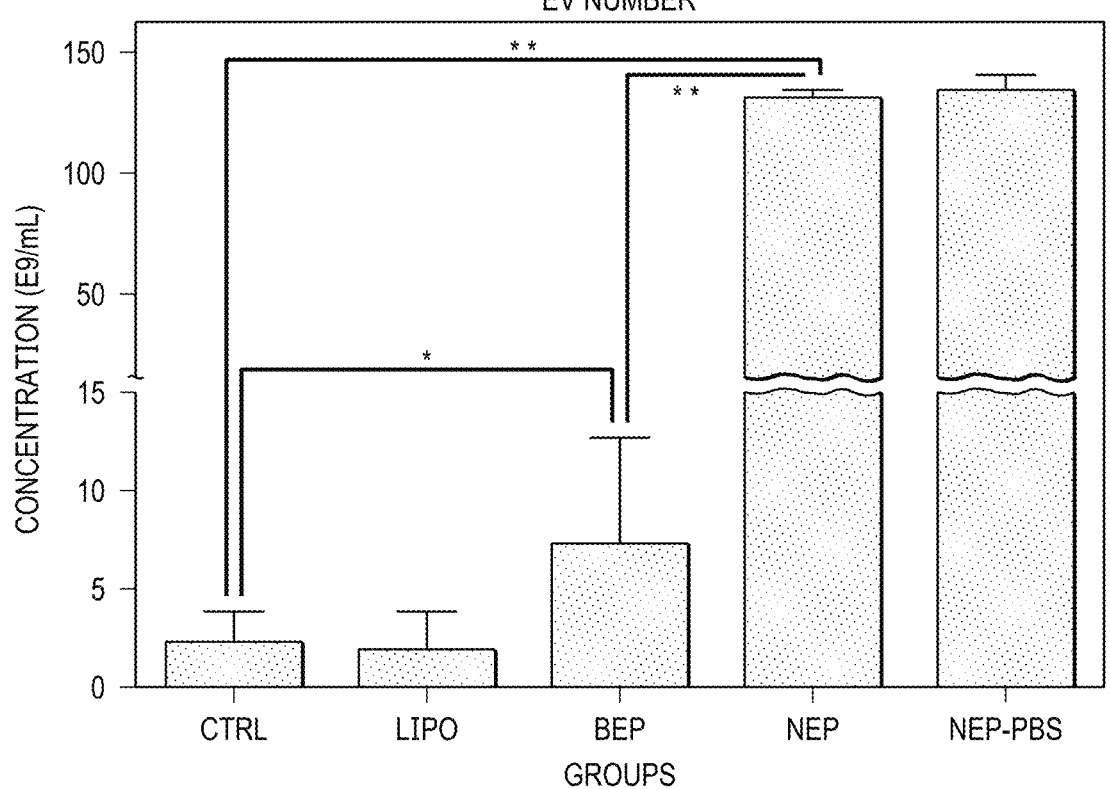
FIG. 3 shows that NEP cell transfection with or without DNA plasmids significantly stimulates the EV secretion from transfected mouse embryonic fibroblast (MEF) cells, with performance much better than lipofectamine (Lipo) and BEP based cell transfection. Ctrl stands for non-transfected MEF cells; NEP stands for NEP cell transfection with DNA plasmids; NEP-PBS stands for NEP cell transfection with PBS buffer only. The DNA plasmids used are Achaete-Scute Complex Like-1 (Ascl1), Pou Domain Class 3 Transcription factor 2 (Pou3f2 or Brn2) and Myelin Transcription Factor 1 Like (Myt11) at a weight ratio of 2/1/1. A mixture of those DNA plasmids is known to reprogram donor cells into induced neurons (iNs). The same number of MEF cells were transfected with DNA plasmids by various techniques, and cell culture mediums were collected 24 h post-transfection. The EV numbers were detected by NanoSight™. For the BEP, the transfection voltage was 1250 volts; for NEP, the transfection voltage was 220 volts with five 10 ms pulses.

FIG. 3 compares EV numbers secreted from the same number of MEF cells (5E6 cells) transfected with the same Ascl1, Brn2 and Myt1l DNA plasmids at a weight ratio of 2/1/1 by either lipofectamine (Lipo), BEP or NEP. All EVs were collected from cell culture medium at 24 h post-transfection and the total EV number was determined by NanoSight™. For BEP, the transfection voltage was 1250 v with one 30-ms pulse. For NEP, the transfection voltage was 220 with five 10 ms pulses. The concentration of plasmid used was Ascl1/Brn2/Myt1l=200/100/100 ng/μl. For lipofectamine transfection, 5 μg plasmid mixture (Ascl1/Brn2/Myt1l=2/1/1) was used according to manufacturer's instruction. The EVs were collected from cell culture medium by simply centrifugation at 1500 g for 10 mins. The results show that lipofectamine (Lipo) based cell transfection did not change the EV secretion. The EV concentration was around 2E9/ml with or without transfection. Apparently, a slow plasmid endocytosis process by nanoparticle carriers would not stimulate the transfected cells much and, consequently, there was almost no change on EV secretion. In comparison, BEP based cell transfection led to more EV secretion to ~6E9/ml. A tremendous increase of EV secretion to >1.3E11/ml was observed by NEP cell transfection with or without adding plasmids. This implies that the transfected cells were somewhat stimulated by BEP, but highly stimulated by NEP leading to very significant increase of EVs in the latter case.

Figure 4:
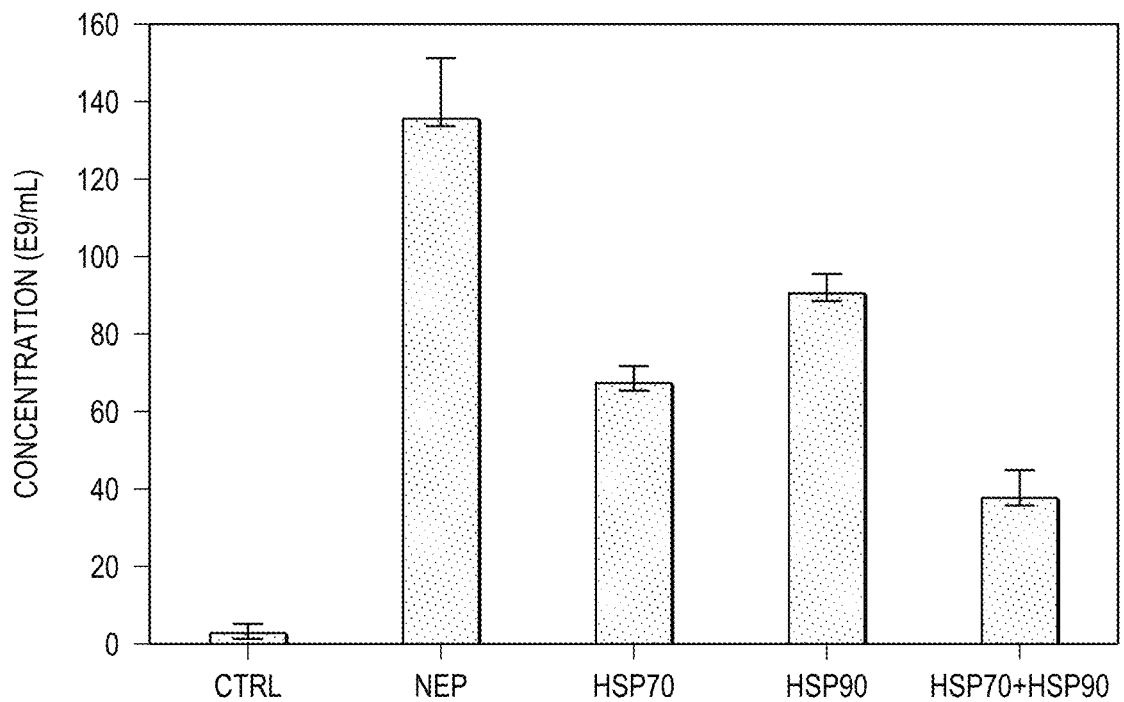
FIG. 4 shows the effect of heat shock protein 70 (HSP70) and heat shock protein 90 (HSP90) inhibitors on EV secretion from NEP transfected MEF cells. After NEP transfection, the cell culture was replaced with fresh medium containing HSP70 inhibitor (VER 155008, 50 µM), HSP90 inhibitor (NVP-HSP990, 1 µM), or their mixture. Medium was collected at 24 h post-transfection, and EV numbers were detected by dynamic light scattering (DLS) goniometry.

During electroporation, Joule heating caused by the imposed electric field could tentatively increase the cell temperature to cause thermal shocking to the transfected cells. It is known that thermal shocking may increase cell secretion of EVs due to chaperone mediated autophage caused by the increase of heat shock proteins in cells (8-10). Indeed, we found that NEP could substantially increase the expression of both heat shock protein 70 (HSP70) by 13.8 folds and heat shock protein 90 (HSP90) by 4.2 folds in the transfected MEF cells vs. the non-transfected MEF cells (Ctrl). When HSP inhibitors were added in cell culture medium after electroporation, EV secretion could be suppressed. FIG. 4 shows 50%, 40% and 70% decrease of EV secretion of NEP transfected MEF cells with HSP 70 inhibitor (VER 155008, 50 μM) HSP90 inhibitor (NVP-HSP990, 1 μM), and their mixture respectively. Here, the cell culture was replaced with fresh medium containing HSP70 inhibitor (VER 155008), HSP90 inhibitor (NVP-HSP990), or their mixture right after NEP transfection. Medium was collected at 24 h post-transfection and EV numbers were detected by dynamic light scattering (DLS) goniometry. These results imply that any cell stimulation that can increase the expression of heat shock proteins would enhance EV secretion.

Figure 5:
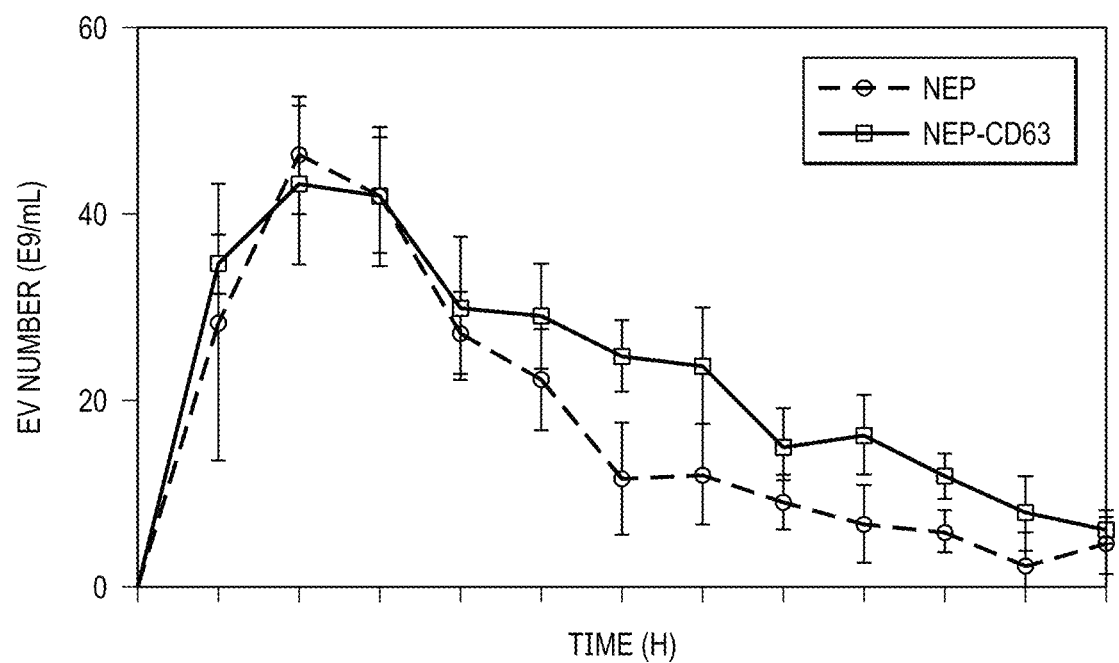
FIG. 5 shows the effect of NEP transfection of CD63 DNA plasmid on EV secretion from MEF cells. Cells were transfected with or without CD63 plasmid by NEP. The cell culture medium was collected and replaced with fresh medium every 4 hr. The EV numbers were detected by DLS goniometry.

Similarly, an increase of proteins that are needed for late endosomal multi-vescular body (MVB) formation in cells may also enhance exosome secretion. FIG. 5 shows the effect of NEP transfection of CD63 DNA plasmid on EV secretion from MEF cells. Cells were transfected with or without CD63 DNA plasmid by NEP. The cell culture medium was collected and replaced with fresh medium every 4 h. The EV numbers were detected by DLS goniometry. The results show a similar EV secretion profile during the first 16 h after NEP transfection in both cases. However, more EVs were secreted between 16 to 44 h after NEP transfection with CD63 DNA plasmid. CD63 protein is essential for the reorganization of endosomal membrane into tetraspanin enriched microdomains, a precursor of exosome secretion.

Figure 6A:
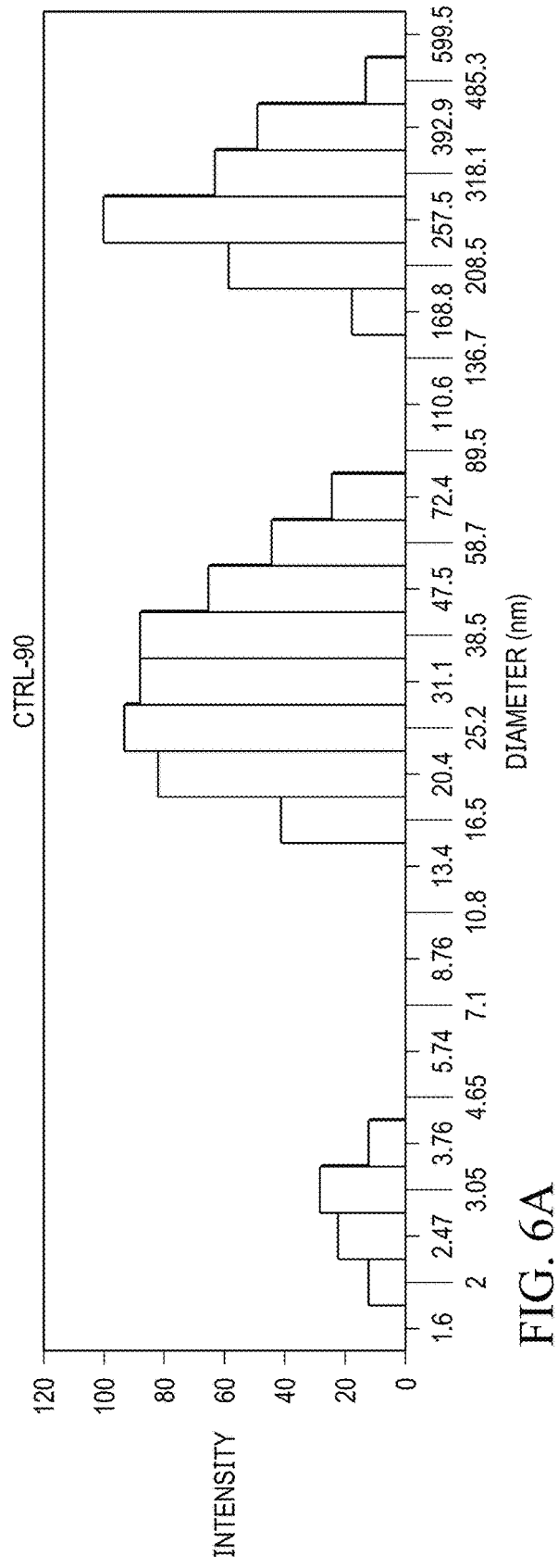
FIG. 6A shows a size distribution measured by DLS goniometery of EVs without NEP harvested at 24 h post-cell transfection.
Figure 6B:
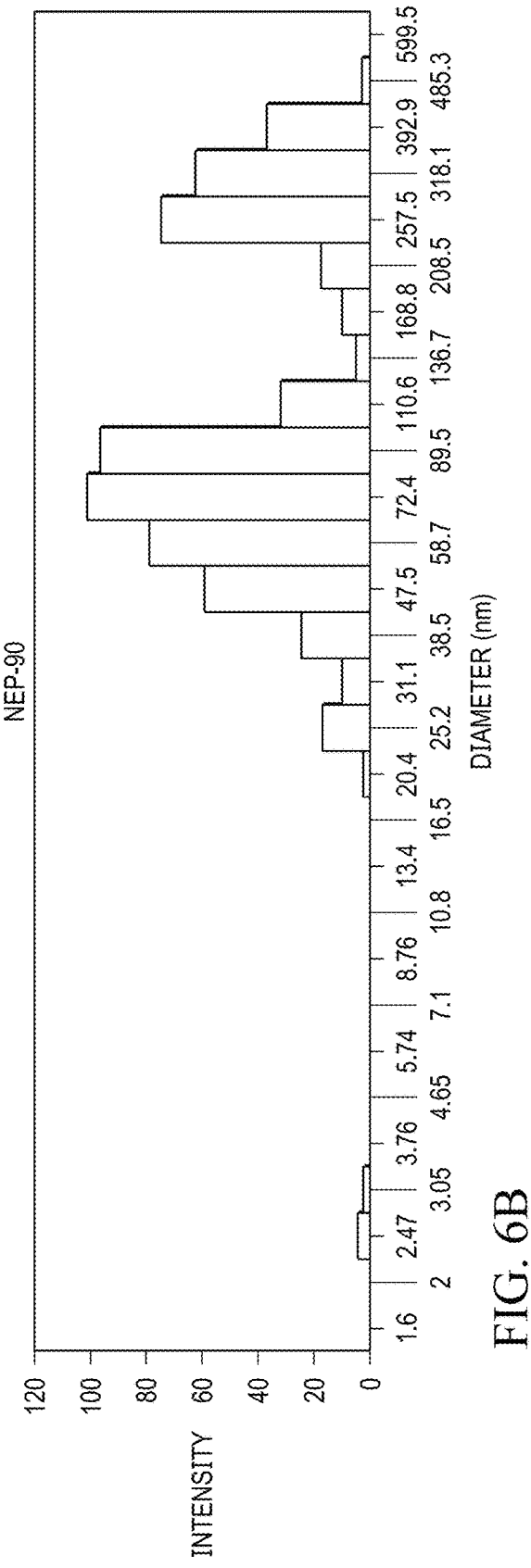
FIG. 6B shows a size distribution measured by DLS goniometery of EVs with NEP harvested at 24 h post-cell transfection, where the cell culture medium was collected 24 h post transfection, where cell debris was removed by centrifugation at 1500 g for 10 min, and the EVs in supernatant were measured by DLS.
Figure 7A:
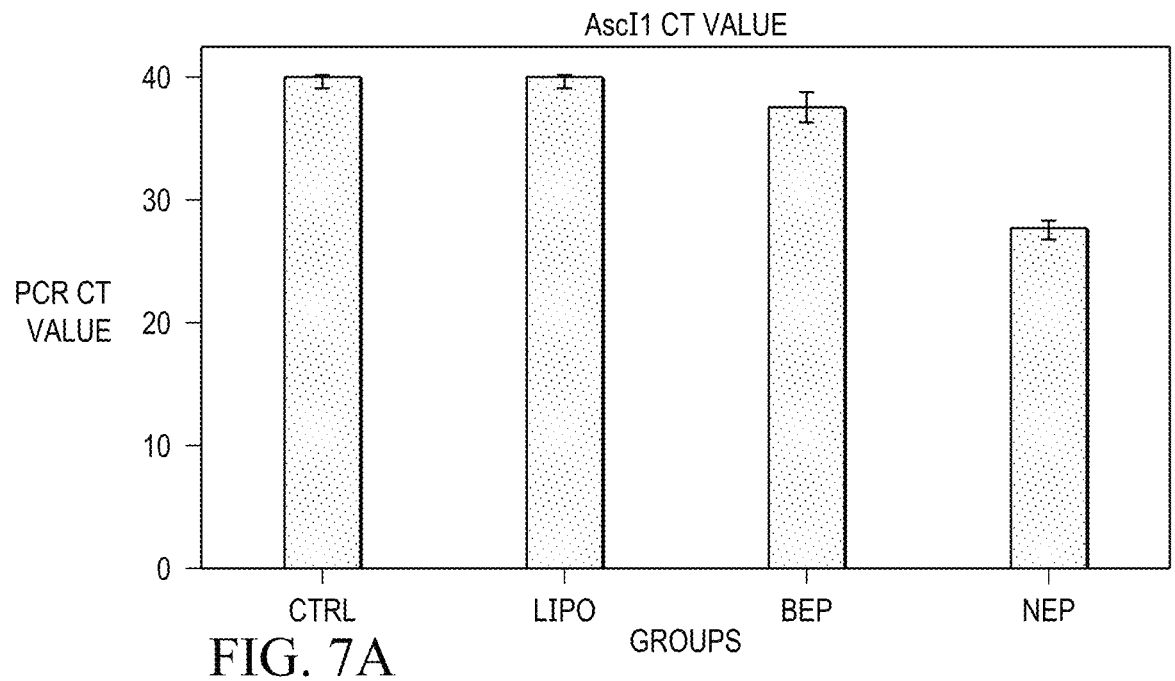
FIGS. 7A and 7B demonstrate EV Ascl1 mRNA expression determined by qRT-PCR from MEF cells transfected by Ascl1/Brn2/Myt11 DNA plasmids at a ratio of 2/1/1 using various techniques at 24 h post-transfection, with total RNAs obtained and reverse transcript, according to manufacturer's instructions, where the same amount of total RNA (2ong) used for Ascl1 detection by qRT-PCR.
Figure 7B:
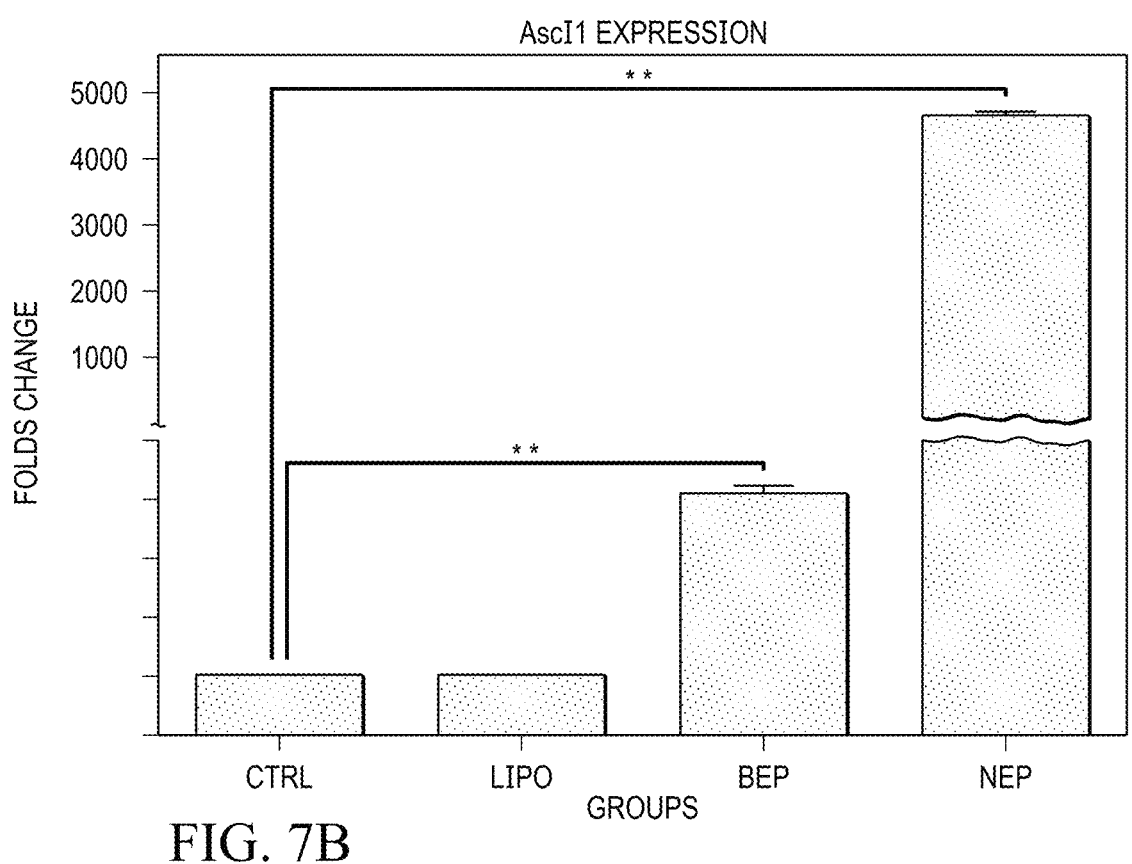
Figure 8A:
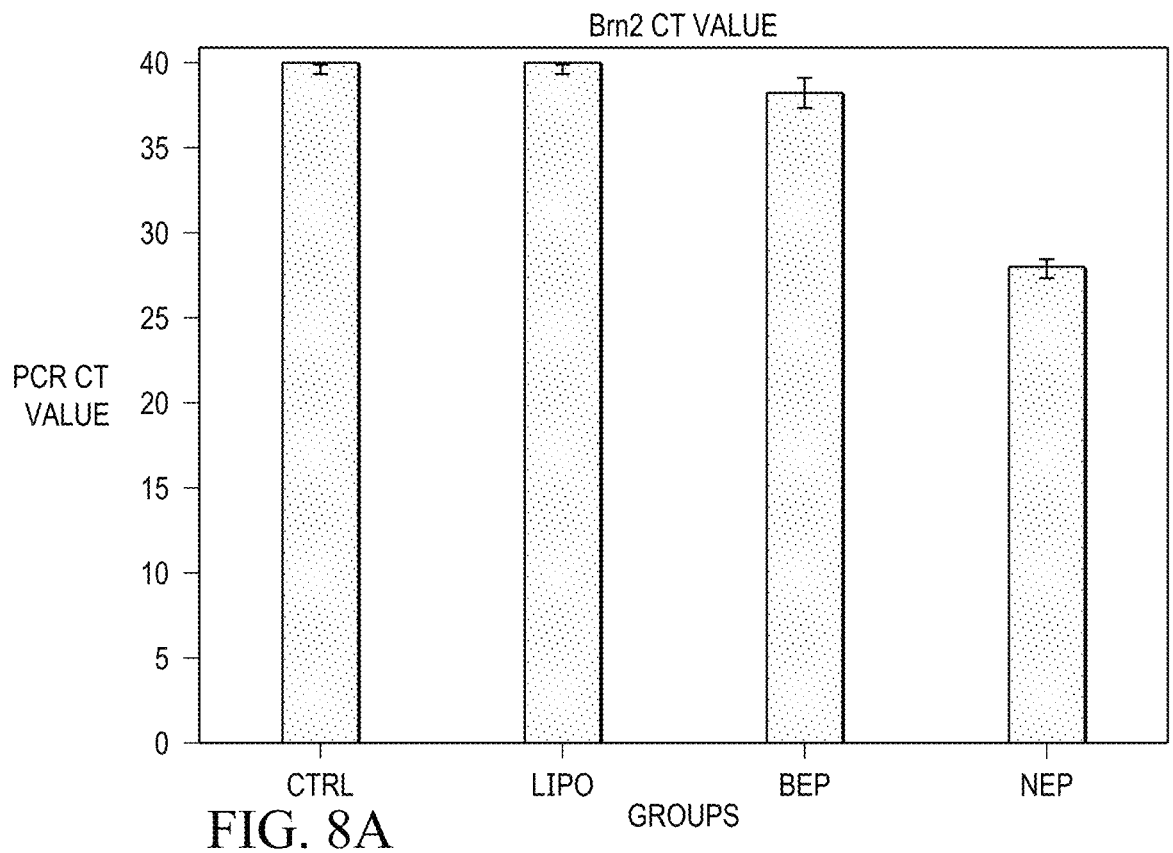
FIGS. 8A and 8B show EV Brn2 mRNA expression determined by qRT-PCR from MEF cells transfected by Ascl1/Brn2/Myt11 DNA plasmids at a ratio of 2/1/1 using various techniques at 24 h post-transfection, with total RNAs obtained and reverse transcript, according to manufacturer's instructions, where the same amount of total RNA (20 ng) used for Ascl1 detection by qRT-PCR.
Figure 8B:
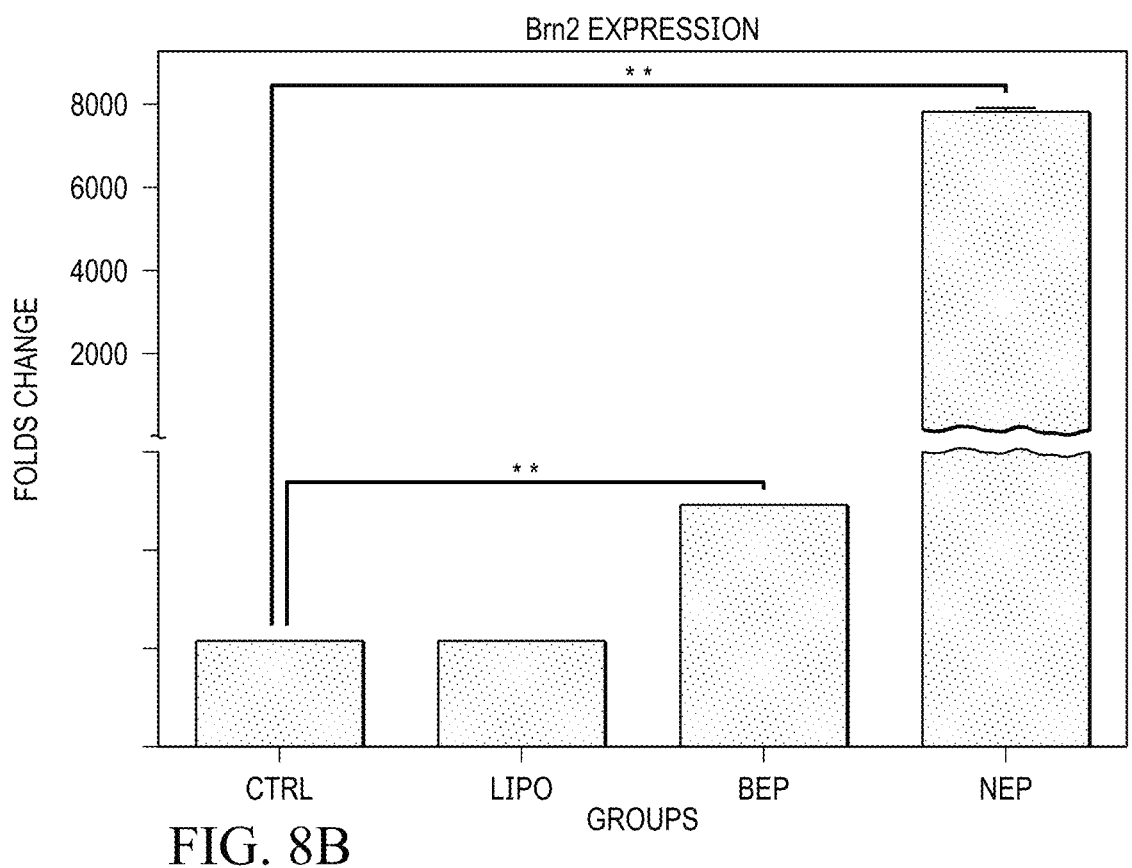
Figure 9A:
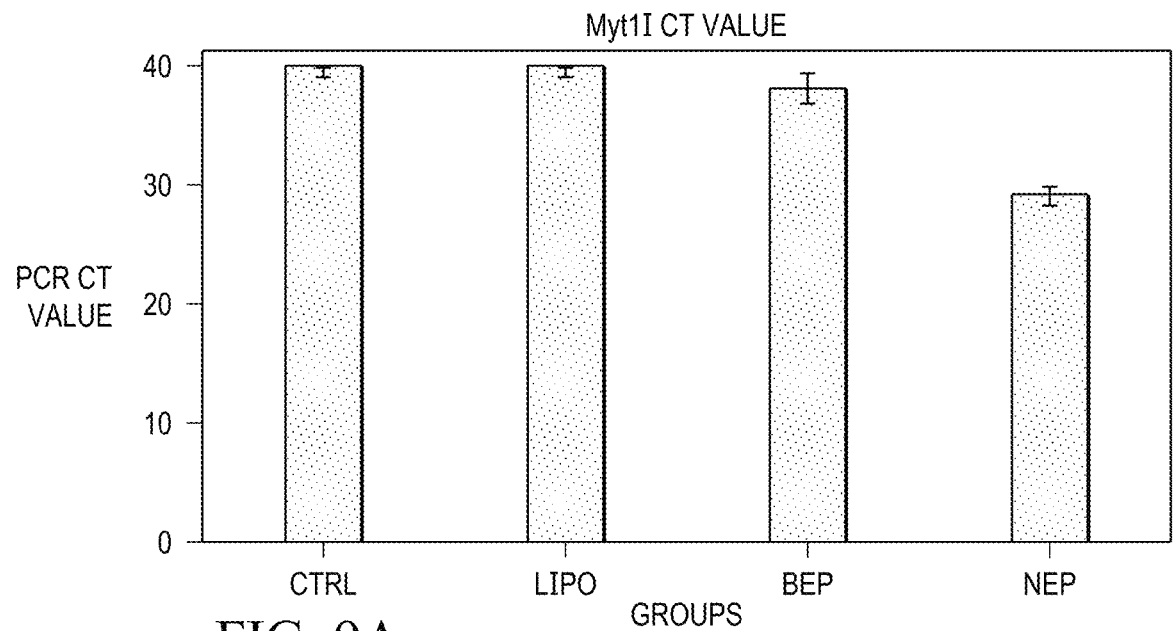
FIGS. 9A and 9B show EV Myt11 mRNA expression determined by qRT-PCR from MEF cells transfected by Ascl1/Brn2/Myt11 DNA plasmids at a ratio of 2/1/1 using various techniques at 24 h post-transfection, with total RNAs obtained and reverse transcript, according to manufacturer's instructions, where the same amount of total RNA (20 ng) used for Ascl1 detection by qRT-PCR.
Figure 9B:
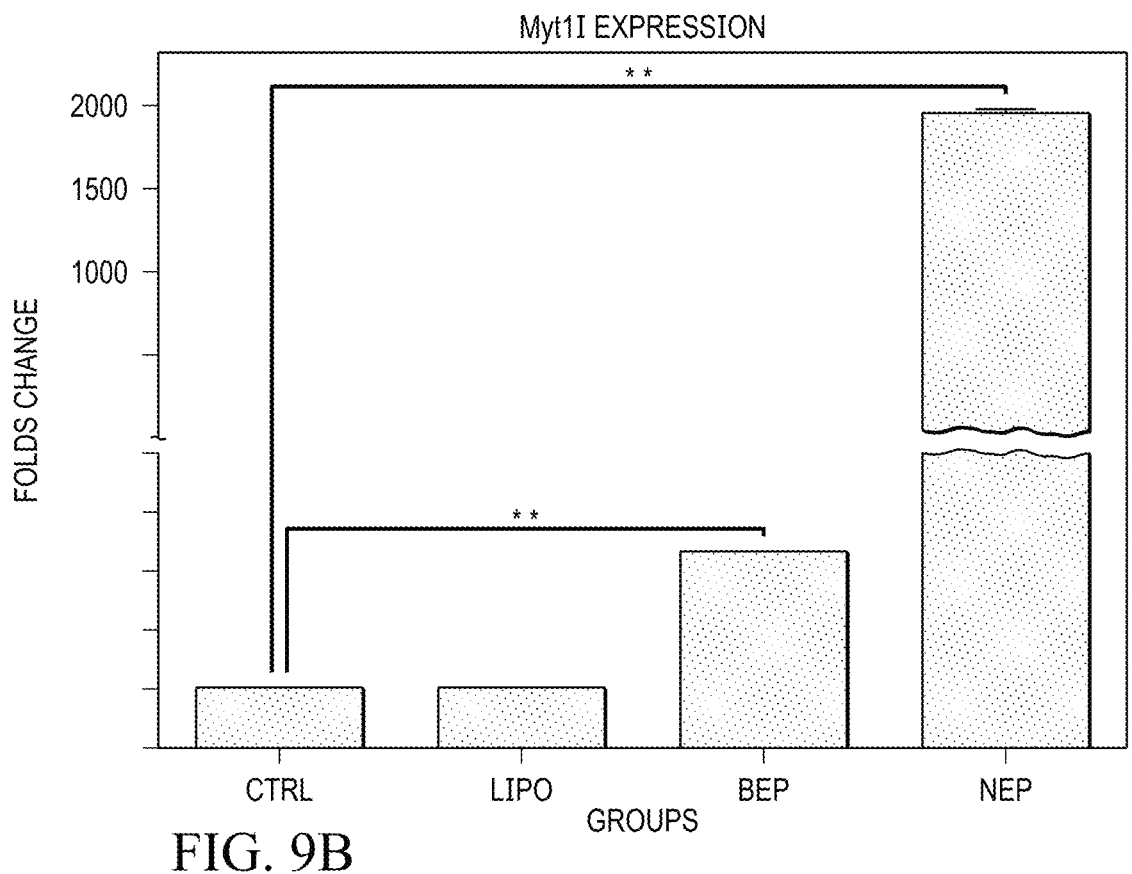

FIGS. 6A and 6B show the EV size distribution measured by DLS goniometry for MEFs (ctrl) and NEP transfected MEFs. NEP stimulation did not change the larger EV (mostly microvesicles) distribution much, but substantially increased the secretion of exosomes with sizes ranging from 40 to 110 nm.

FIGS. 8A, 8B, 9A and 9B show that the secreted EVs from NEP cell transfection of Ascl1, Brn2 and Myt11 DNA plasmids contain a large amount of corresponding Ascl1, Brn2 and Myt11 mRNAs or their fragments as determined using quantitative-Reverse Transcription Polymerase Chain Reaction (qRT-PCR). Like the EV numbers, lipofectamine (Lipo) based cell transfection did not change the mRNA expression much, while the BEP based cell transfection could increase the mRNA expression several folds. In comparison, the NEP based cell transfection resulted in thousands folds increase of target mRNAs. Here, the same amount of total RNAs were obtained and reverse transcription was conducted by qRT-PCR according to manufacturer's instruction.

Figure 10:
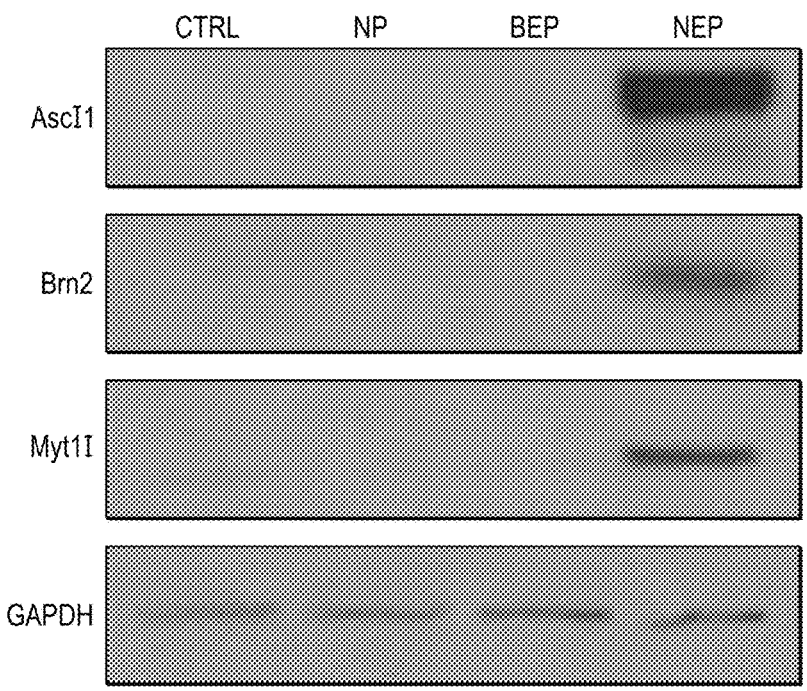
FIG. 10 shows that only EVs obtained by NEP contain functional mRNA determined by in vitro translation, where the same amount of total RNAs (1 µg) from each transfection group was used for in vitro protein translation according to manufacturer's instruction, and where the samples were separated by SDS-Page, and the proteins were detected with antibodies.

FIG. 10 shows that some of the EV mRNAs were intact and functional because they were able to translate Ascl1, Brn2 and Myt11 proteins. Here, a same amount of total RNA (1 µg) from each transfection method was applied for in vitro protein translation using Rabbit Reticulocyte Lysate System (Promega) according to manufacturer's instruction. Samples were separated by SDS-PAGE and the proteins were detected with various antibodies as shown in the Western blotting plot.

Figure 12:
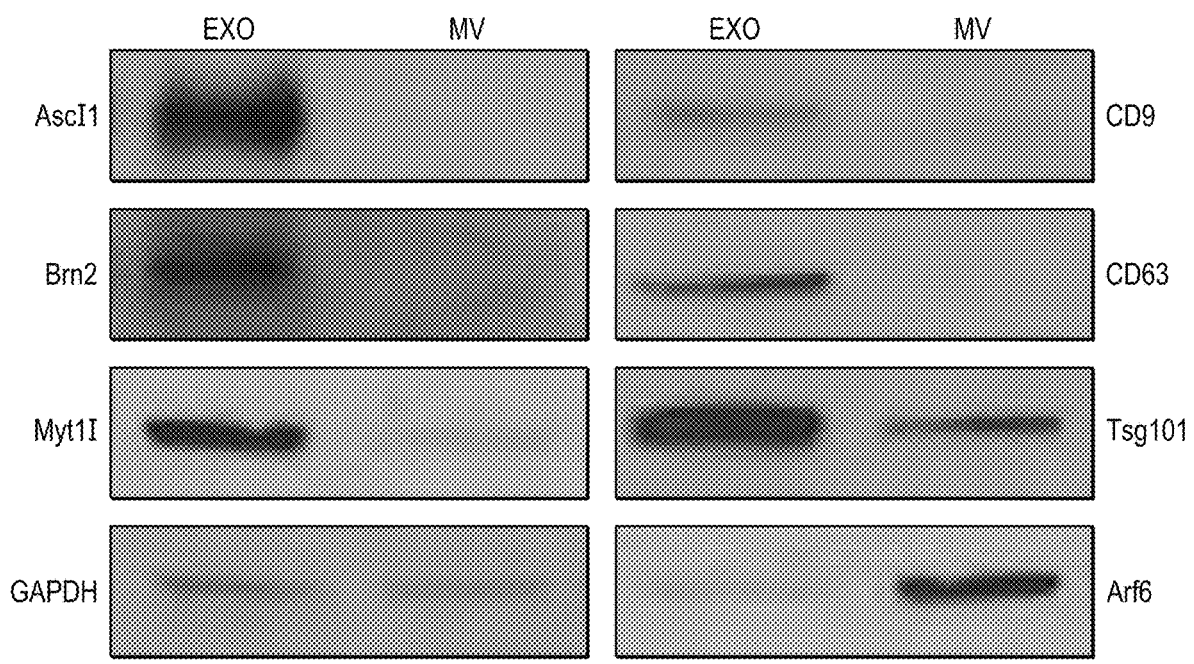
FIG. 12 shows that exosome-mRNAs, not microvesicle-RNAs, from NEP cell transfection can translate proteins. EVs were collected from cell culture medium by simple centrifugation at 1500 g for 10 min. Microvesicles were harvested by ultracentrifugation at 10,000 g for 30 min. The supernatant was further centrifugated at 100,000 g for 2 h to collect the exosomes. Total RNAs were collected from these two parts and 1 μg of total RNA was used for in vitro translation. The samples were separated by SDS-PAGE, and the proteins, exosomes and microvesicle markers were detected by Western blotting.
Figure 11:
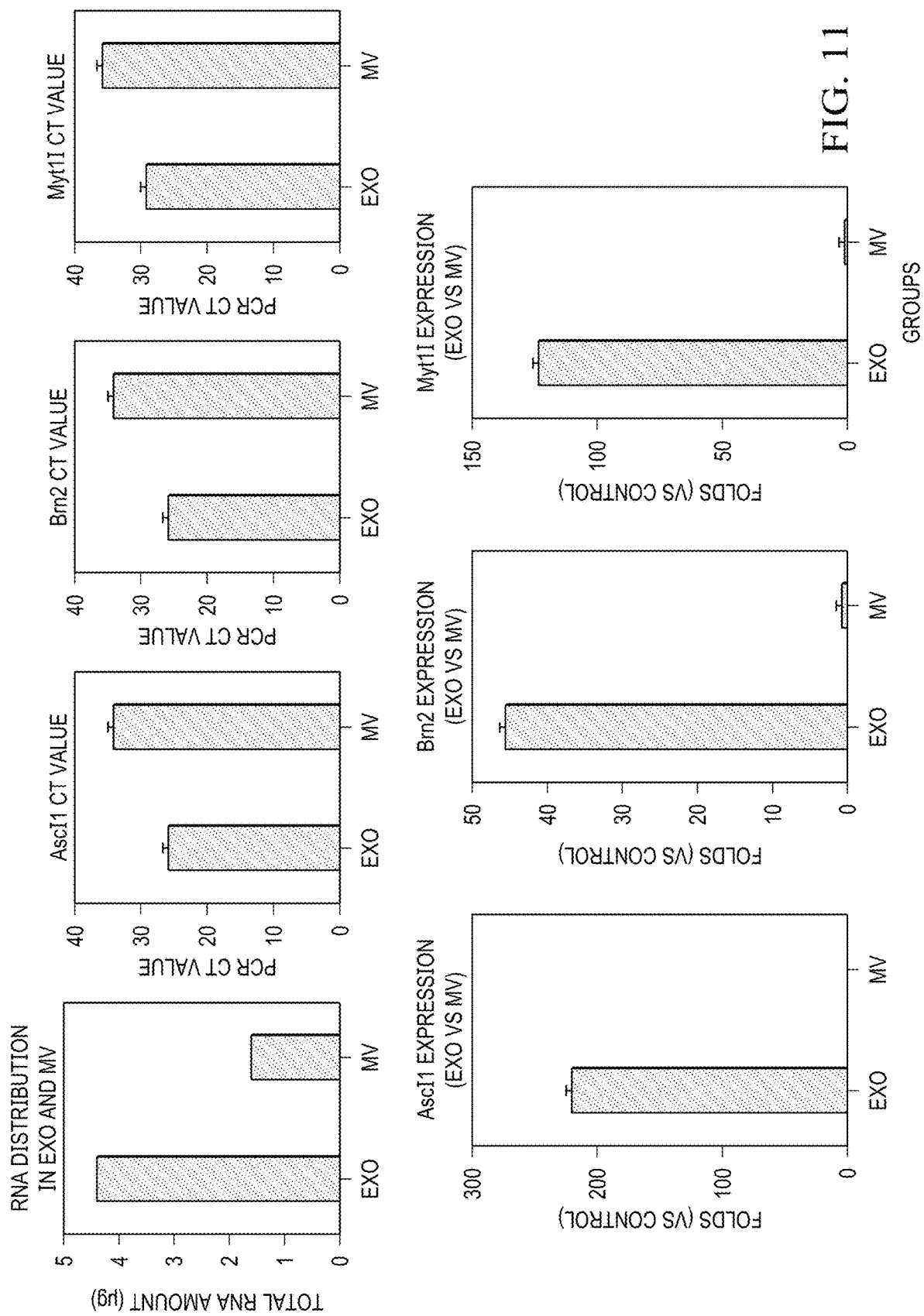
FIG. 11 shows that EV-mRNAs from NEP are found in exosomes (Exo), and not in microvesicles (MV). EVs were collected from cell culture medium by simply centrifugation at 1500 g for 10 min. Microvesicles were harvested by ultracentrifugation at 10,000 g for 30 min. The supernatant was further centrifuged at 100,000 g for 2 h to collect the exosomes. Total RNAs were collected from these two parts and the total mRNA concentration was measured by Nanodrop™. The EV mRNA expressions were measured by qRT-PCR.

For the collected total EVs, the larger microvesicles were sorted by ultracentifugation at 10,000 g for 30 min. The supernatant was further centrifugated at 100,000 g for 2 h to collect the smaller exosomes. Total RNAs were collected from these two parts as described above. The total mRNA concentration was measured by Nanodrop™, while the ABM expressions of Ascl1, Brn2 and Myt11 mRNAs were measured by qRT-PCR. FIG. 11 shows that there was more than twice RNA in exosomes than in microvesicles, but most Ascl1, Brn2 and Myt11 mRNAs were presented only in exosomes. FIG. 12 shows that the functional Ascl1, Brn2 and Myt11 mRNAs were also presented in exosomes and those exosomes carry typical exosomal protein markers, CD9, CD63 and Tsg101. In comparison, the larger microvesicles carry the typical protein marker, Arf6.

Figure 13:
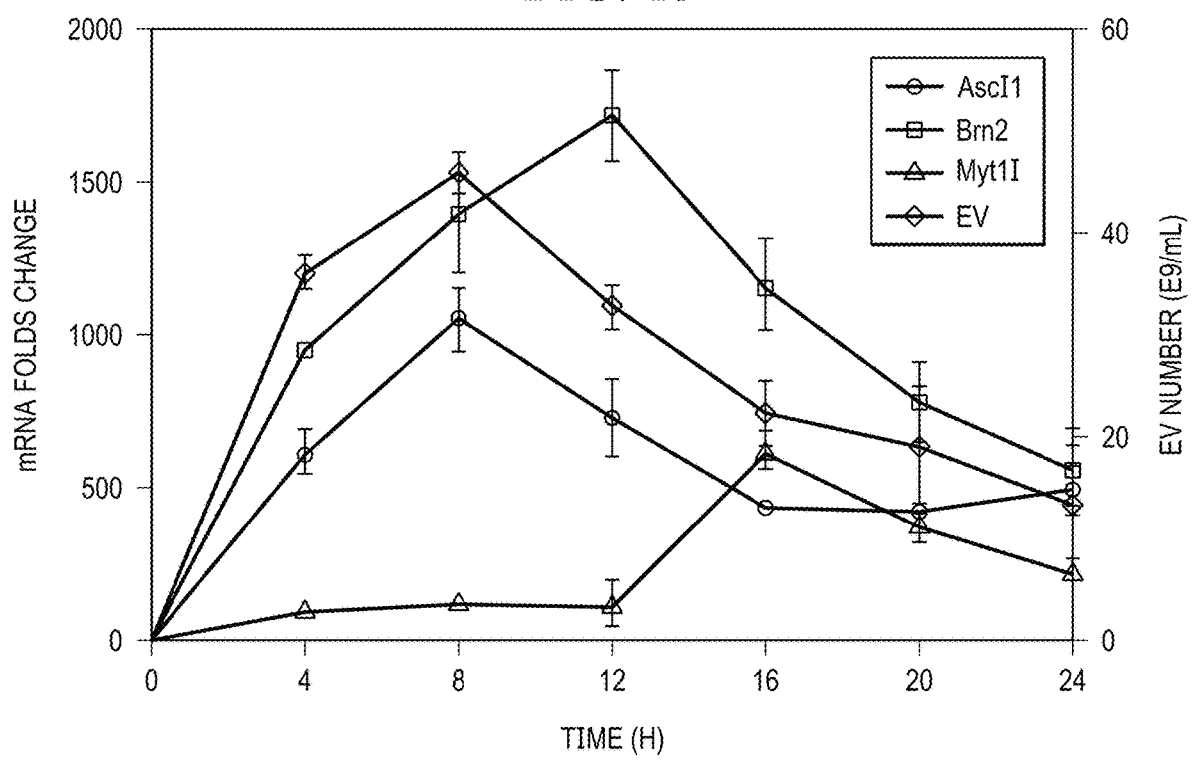
FIG. 13 shows EV-mRNAs secretion profiles from NEP transfected MEF cells, where MEF cells were transfected with DNA plasmids by NEP, where the cell culture medium was collected at indicated time points, and replaced with fresh medium. The EV numbers were detected by DLD goniometry and the mRNA expressions were detected by qRT-PCR.

FIG. 13 shows the EV secretion and content profiles as a function of time after NEP transfection with Ascl1, Brn2 and Myt11 DNA plasmids. The Ascl1 plasmid is the smallest one (7 k bp) among the three, while the Myt11 plasmid is the largest (9 k bp) with the Brn2 plasmid in between (8 k bp).

EVs in the cell culture medium was collected at the indicated time points, and the culture medium was replaced with fresh medium. The EV numbers were detected by DLS goniometry, while the EV mRNA expressions were detected by qRT-PCR as described before. The results show a quick increase of EV secretion within 4 h post-transfection, and peaked at 8 h with continuous EV secretion for more than 24 h. EVs containing Ascl1 and Brn2 mRNAs also appeared within 4 h post-transfection with profiles matching well with that of EV secretion. EVs containing Myt11 mRNA appeared at a later time, but still within 24 h. This implies that the EV secretion time and the mRNA transcription time need to be matched in cell, which can be achieved by NEP based cell transfection.

Figure 14:
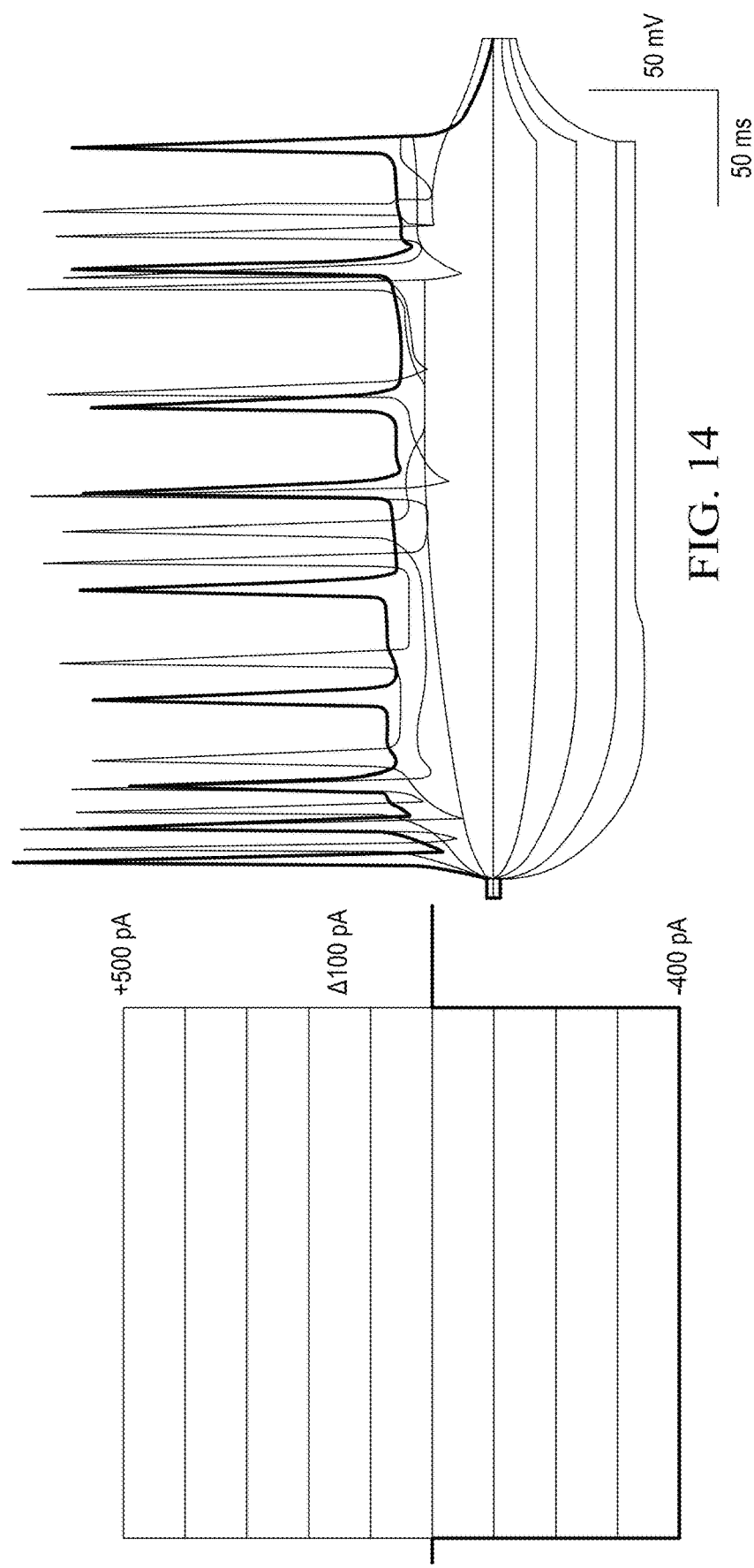
FIG. 14 depicts action potential detection by patch clamp shows that MEF cells transfected every other day with Ascl1/Brn2/Myt1l mRNA containing EVs obtained from NEP could be reprogrammed into functional induced neurons (iNs) after 24 days. NEP-transfected MEF cells were reprogrammed into iNs after 21 days.

To demonstrate that NEP-produced-EVs containing endogenous mRNAs have therapeutic functions, we treated MEF cells with those EVs every other day at a total EV RNA concentration of 1 µg per 100,000 cells. After several days, the treated MEF cells started to reveal neuron-like morphology and at 24 days, the treated cells showed electrophysiological activity as demonstrated by their capacity to undergo induced action potentials as shown in FIG. 14. In comparison, the NEP-transfected MEF cells also showed a similar electrophysiological activity on Day 21. Cells displayed the necessary voltage-gated currents to fire action potentials. Both transient inward currents and sustained outward currents were observed in response to depolarizing voltage simulations. A typical response to a 20 pA current injection is illustrated in FIG. 14 and indicates that cells fired action potentials in response to depolarizing current.

Whole-cell patch clamp recording was used to measure excitability. Cells were continuously superfused with an extracellular bath solution containing 115 mM NaCl, 2 mM KCl, 1.5 mM $MgCl_2$, 3 mM $CaCl_2$, 10 mM HEPES, and 10 mM Glucose (pH 7.4). Glass electrodes (3-4 MΩ) were filled with a pipette solution containing 115 mM K-gluconate, 10 mM N-2-Hydroxyethylpiperazine-N'-2-Ethanesulfonic Acid (HEPES), 4 mM NaCl, 0.5 mM ethylene glycol tetraacetic acid (EGTA), 1.5 mM $MgCl_2$, (pH 7.3). Cells had a patch resistance of >100 MOhm after whole-cell access was gained, and series resistance was compensated 40-50%. Data were collected using an Axopatch 200B amplifier, Digidata 1322A digitizer, and Clampex 9 software (Molecular Devices, Sunnyvale, CA). For analysis of voltage-gated currents, the basal holding potential was −70 mV and cells were stepped for 400 ms in 10 mV increments from −120 mV to 80 mV. Transient inward currents, due to activity of voltage-gated sodium channels, were isolated from measuring the peak amplitude. Sustained plateau currents, reflective of voltage-gated potassium currents, were measured as the average of the last 50 ms of the voltage step in the plateau phase of the current. Action potential induction was measured using current clamp. Current was held at 0 pA and then stepped in 20 pA intervals for 1 sec.

Example 2—EV MicroRNA Content Using Different Transfection Methods

Figure 15A:
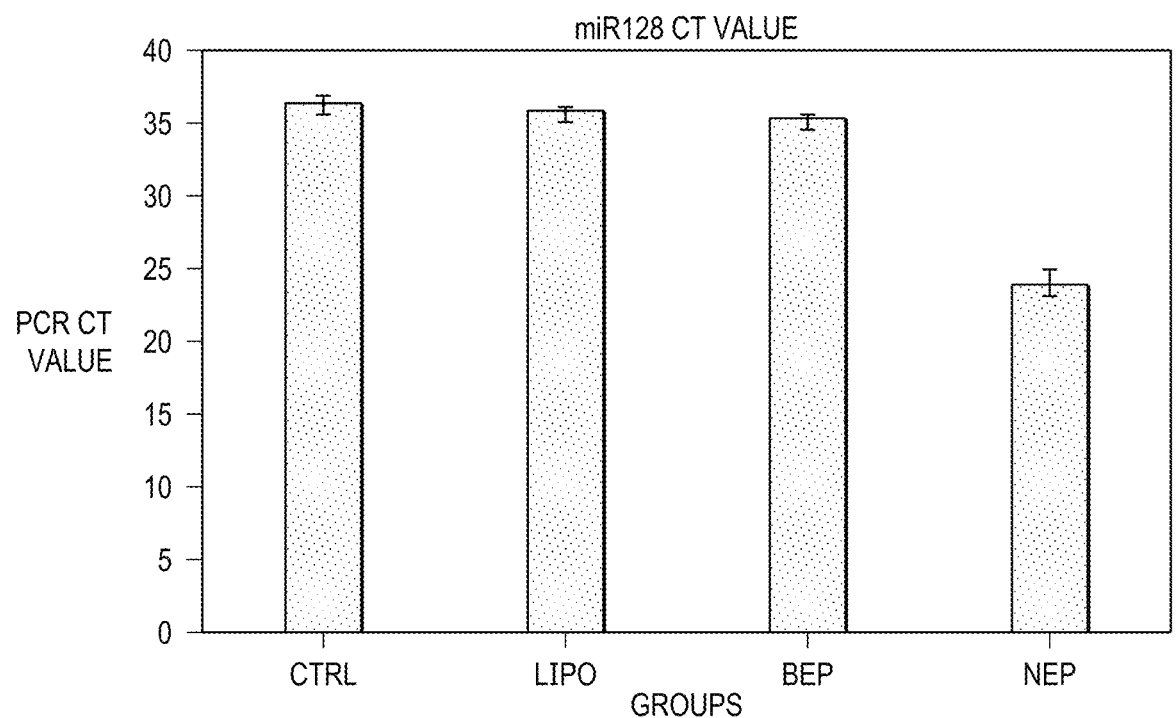
FIGS. 15A and 15B show EV miR-128 expression determined by qRT-PCR from MEF cells transfected by miR-128 DNA plasmid using various techniques at 24 h post-transfection, where EVs were harvested from cell culture medium at 24 h post transfection (miR-128 plasmid) by various techniques, total RNAs were obtained according to manufacturer's instructions, and the same amount of total RNA (30 ng) was used for miR-128 detection by qRT-PCR.
Figure 15B:
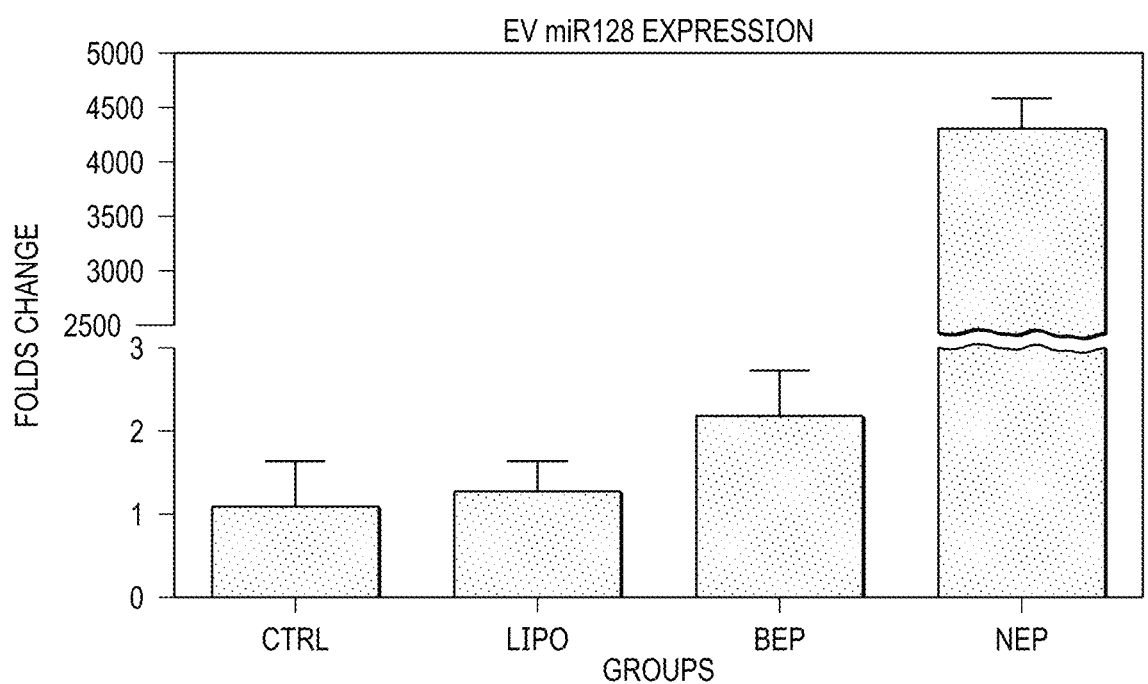

To demonstrate broader therapeutic applicability, we also transfected MEF cells with a DNA plasmid that will transcribe microRNA targets in cells. FIGS. 15A and 15B show the EV miR-128 expression for EVs harvested from cell culture medium at 24 h post-transfection (miR-128 plasmid) by various techniques. Total RNAs were obtained according to manufacturer's instruction. The same amount of total RNA (30 ng) was used for miR-128 detection by qRT-PCR using the aforementioned procedures. Again, NEP based transfection was able to produce EVs containing a large amount of miR-128 (more than 4,500 folds increase), not achievable by BEP or lipofectamine based cell transfection.

Figure 16A:
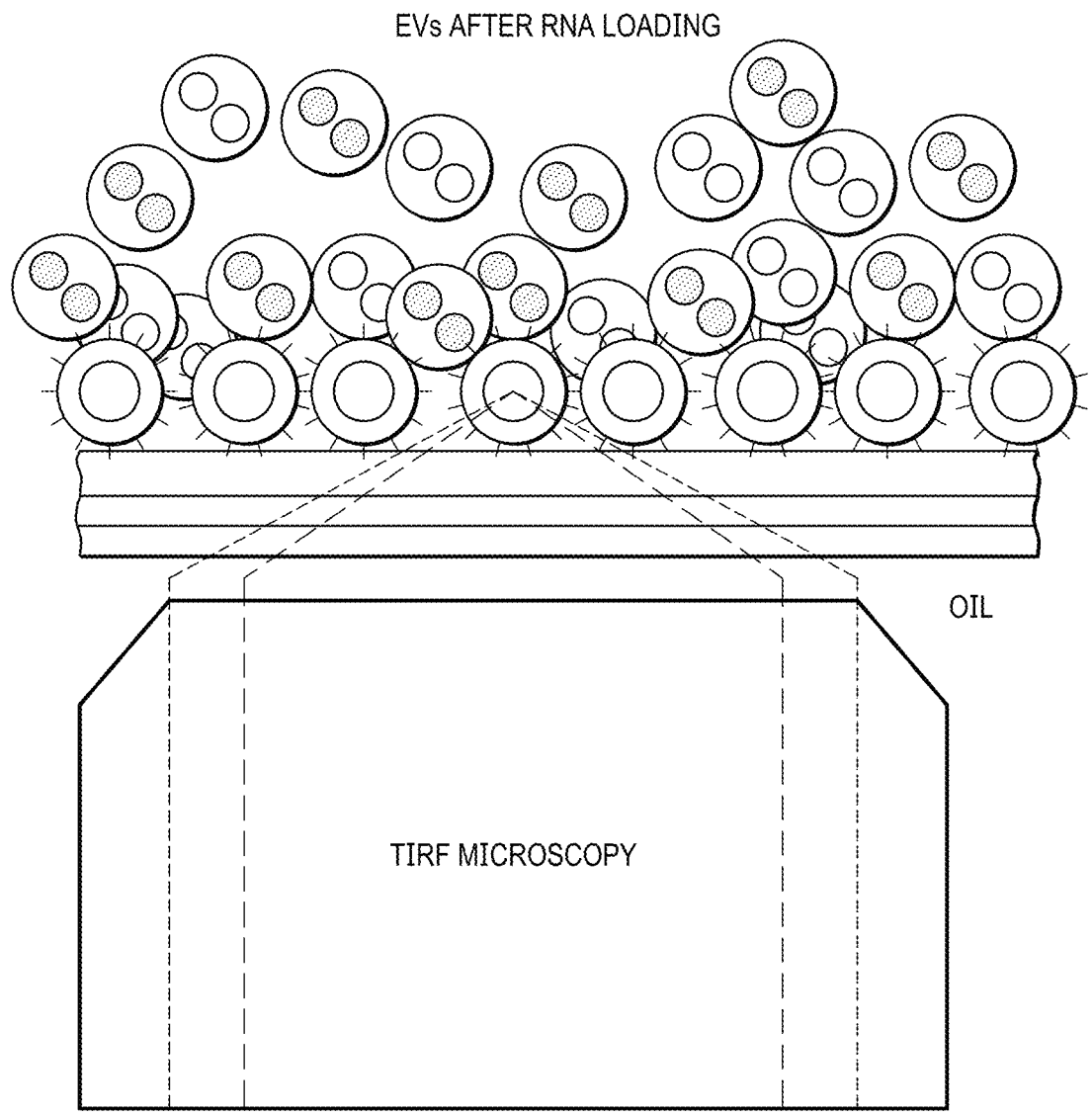

Example 3—Comparison of EVs Containing Endogenous RNAs by NEP Transfection of DNA Plasmid to MEF Cells Vs. Existing EVs Loaded with Pre-Collected RNAs by BEP Post-Insertion Here, we compared the efficacy of producing therapeutic EVs using our NEP based cell transfection and the BEP post-insertion approach used by several researchers. For the former, the miR-128 plasmid was co-transfected with CD63-GFP plasmid to MEF cells by NEP to generate EVs containing miR-128 according to aforementioned procedures. For the latter, blank EVs were first harvested from MEF cells transfected with CD63-GFP plasmid 24 h after NEP. In parallel, miR-128 was collected from MEF cells transfected with miR-128 plasmid 24 h post-transfection by NEP. The collected miR-128 (1 μg) was mixed with blank EVs (10E6) and electroporated by BEP (1250 volts, 30 ms) according to conditions used by other researchers. EVs from the two approaches were tested using a tethered lipoplex nanoparticle (TLN) biochip on a total internal reflection fluorescence (TIRF) microscope. FIG. 16A shows the TLN-TIRF assay schematic (2, 11). Briefly, a molecular beacon (MB) for the RNA target is designed and encapsulated in cationic liposomal nanoparticles. These cationic lipoplex nanoparticles are tethered on a glass slide, which are able to capture negatively charged EVs by electrical static interactions to form a larger nanoscale complex. This lipoplex-EV fusion leads to mixing of RNAs and MBs within the nanoscale confinement near the biochip interface. TIRF microscopy is capable of detecting a single biomolecule and it measures signals <300 nm near the interface, which is where the tethered liposomal nanoparticles locate.

Figure 16B:
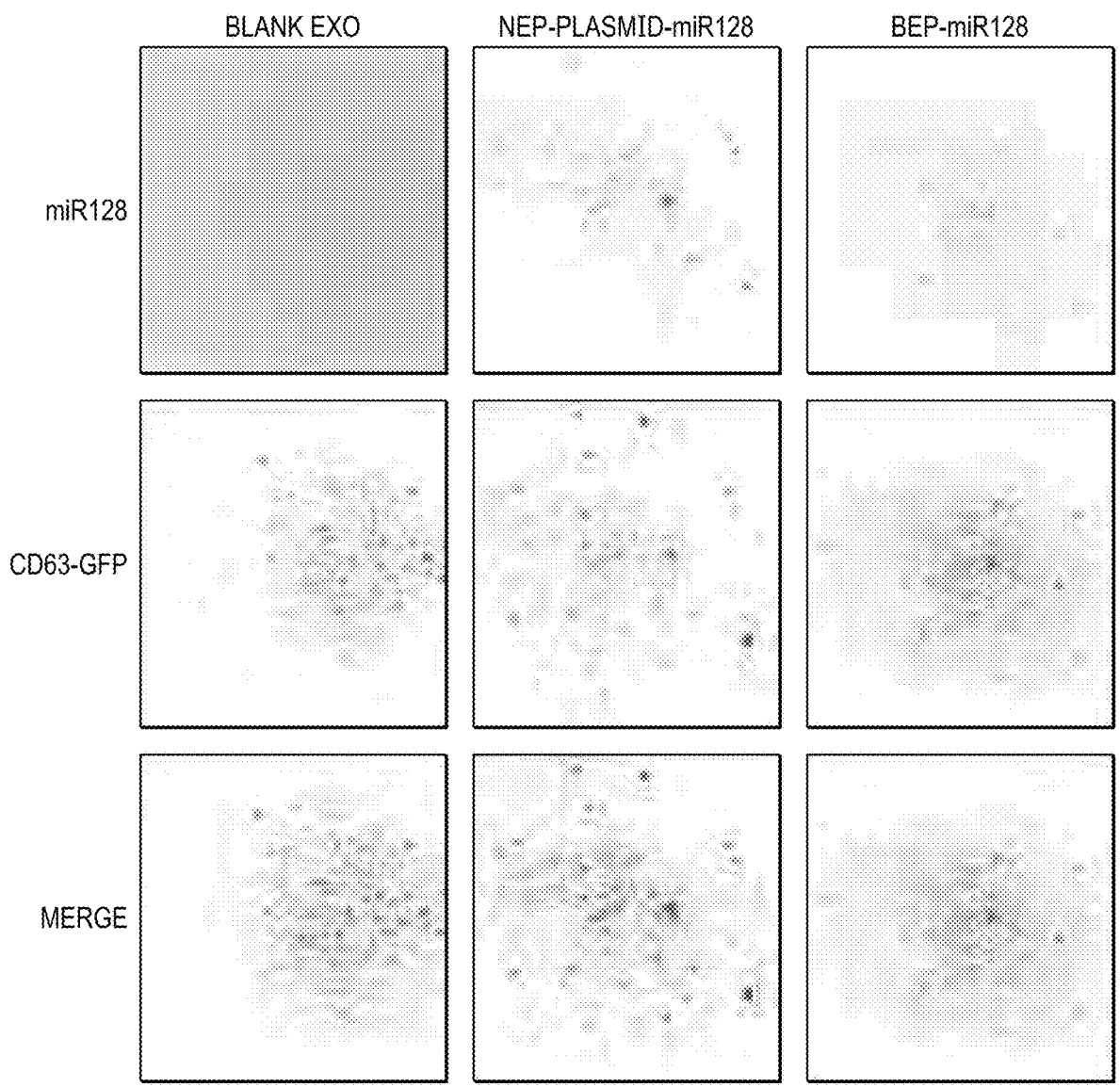
Figure 16C:
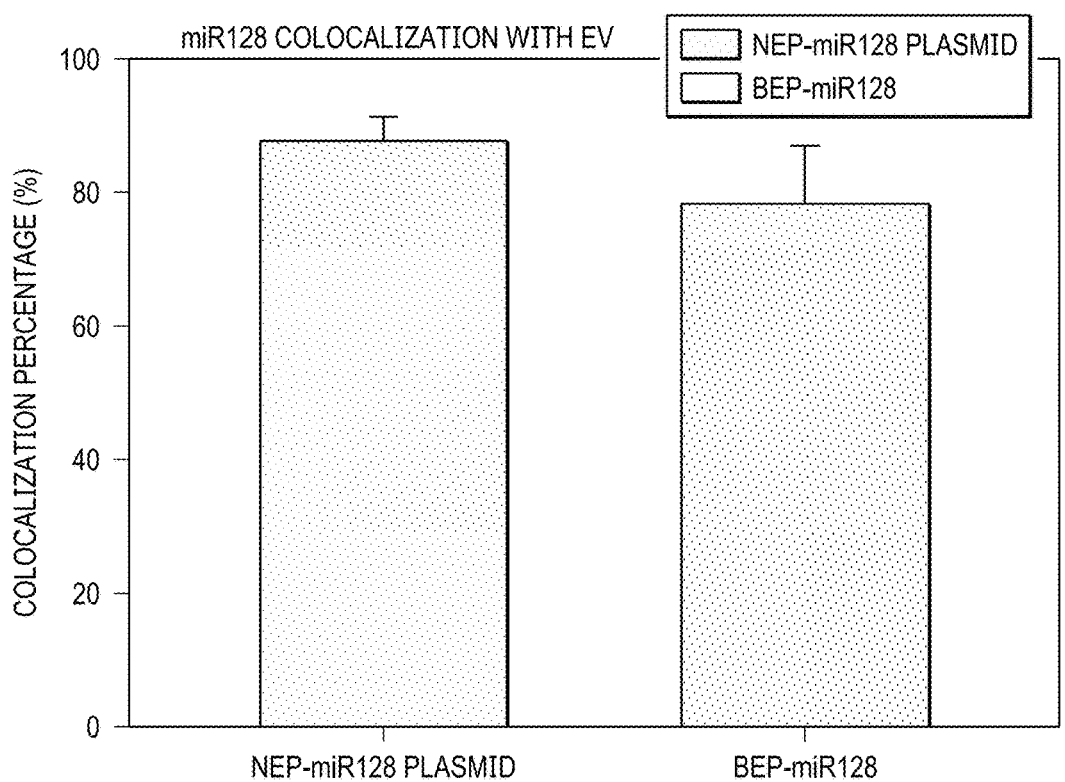
Figure 16D:
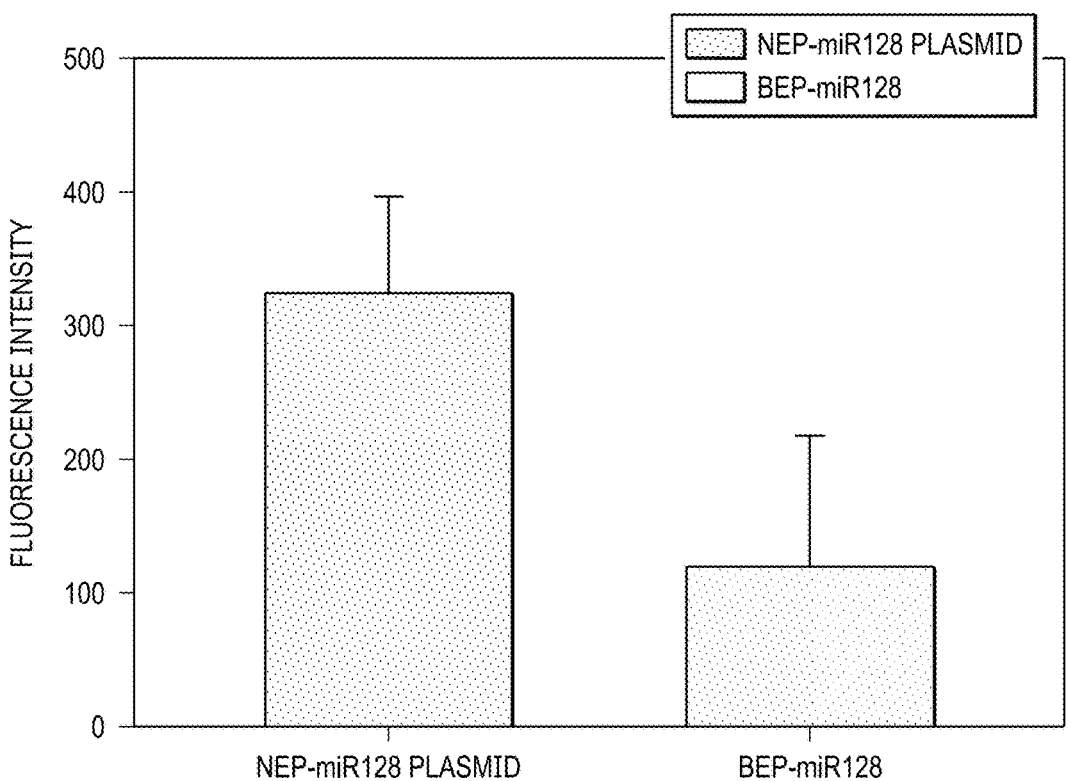

FIG. 16B shows the representative TLN-TIRF images of the captured EVs. The green fluorescence is from EVs containing CD63-GFP, while the red fluorescence is from hybridization of miR-128 molecules and the Cy5-miR128 MBs in the captured EVs. It is clear that our NEP approach is able to produce more EVs containing higher copies of miR-128 than the BEP post-insertion approach. FIGS. 16C-E show a quantitative comparison of those two approaches. Although both approaches are able to produce EVs containing miR-128 (~80% of total captured EVs), the EV miR-128 concentration in EVs (~3 times MB fluorescence intensity) is much higher in NEP based direct cell transfection than in BEP based microRNA post-insertion. Furthermore, BEP post-insertion tends to break nearly half of the blank EVs leading to a very low yield of therapeutic EVs.

Figure 17A:
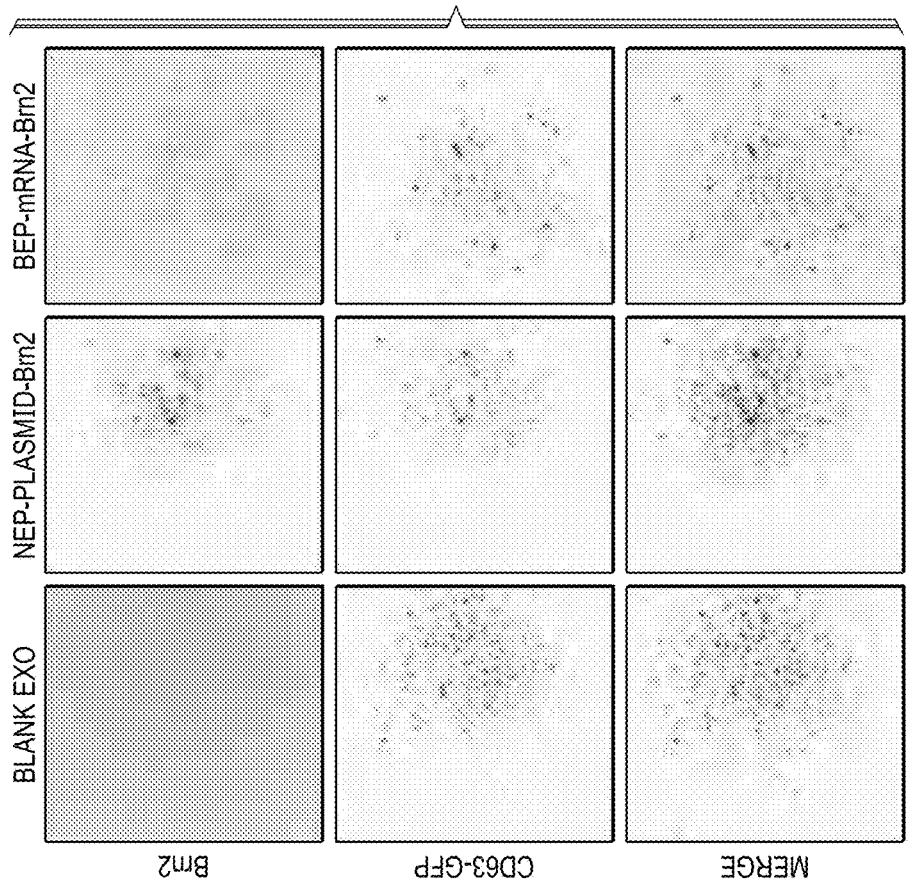
FIGS. 17A to 17C compare secreted EVs containing Brn2 mRNA by NEP transfection of DNA plasmid to MEF cells vs. existing EVs loaded with pre-collected Brn2 mRNA by BEP post-insertion.
Figure 17B:
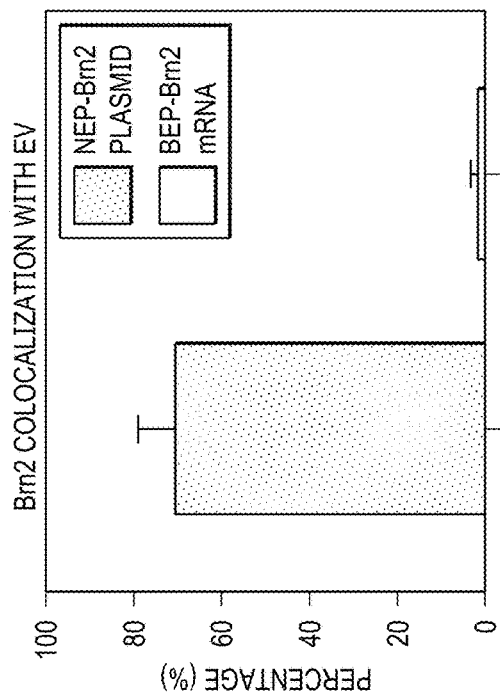
Figure 17C:
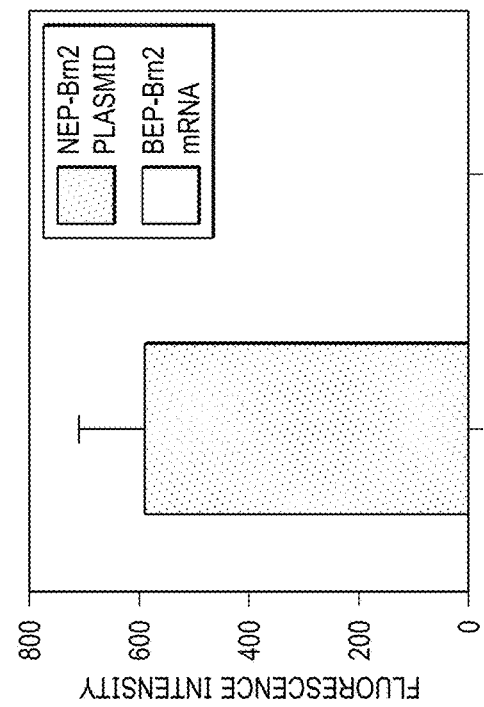

A similar comparison was also carried out for a much larger RNA, Brn2 mRNA (6272 bases for Brn2 mRNA vs. 21 bases for miR-128) using the same approach as for miR-128. FIGS. 17A to 17C shows that our NEP approach could produce >70% EVs containing Brn2 mRNA, while only very few existing EVs could be loaded with the same mRNA by BEP post-insertion approach. The concentration of Brn2 mRNA in NEP produced EVs is high, while that in BEP post-insertion is very poor.

Figure 18:
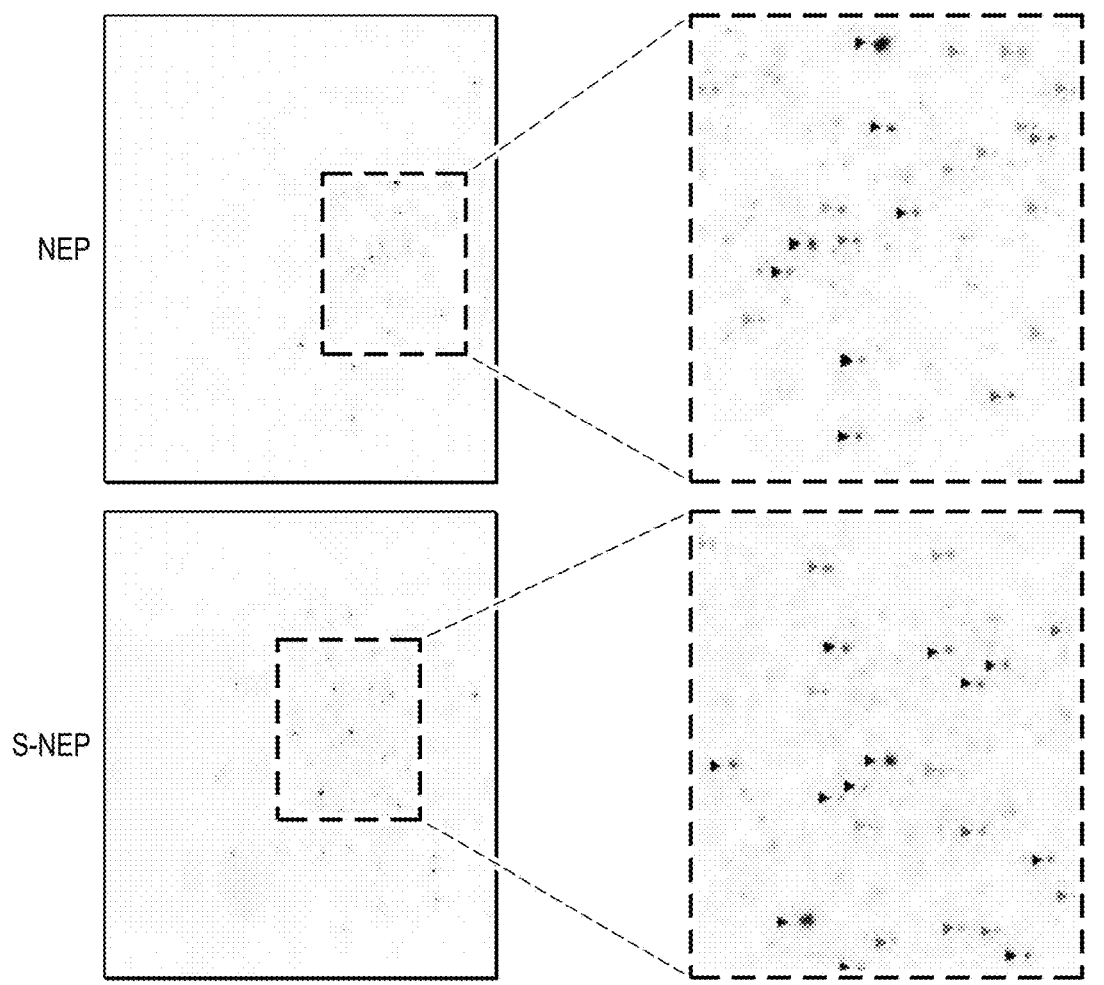
FIG. 18 shows increased mRNA co-localization in the same EV by sequential-NEP. For NEP transfection, Asci1, Brn2 and Myt1l plasmids were transfected at the same time as described before. For sequential-NEP, the Myt1l plasmid was transfected first, Brn2 plasmid was transfected 4 h later, while Ascl1 plasmid was transfected 4 h after Brn2 transfection. At 24 h post Myt1l transfection, culture medium was collected for TLN assay. Equal amount of FAM-Ascl1, Cy3-Brn2, and Cy5-Myt1l MBs were encapsulated in tethered lipoplex nanoparticles for EV-mRNA detection. Yellow arrow: EVs containing 3 mRNAs; Blue arrow: EVs containing 2 mRNAs; and Pink arrow: EVs containing 1 mRNA.
Figure 18:
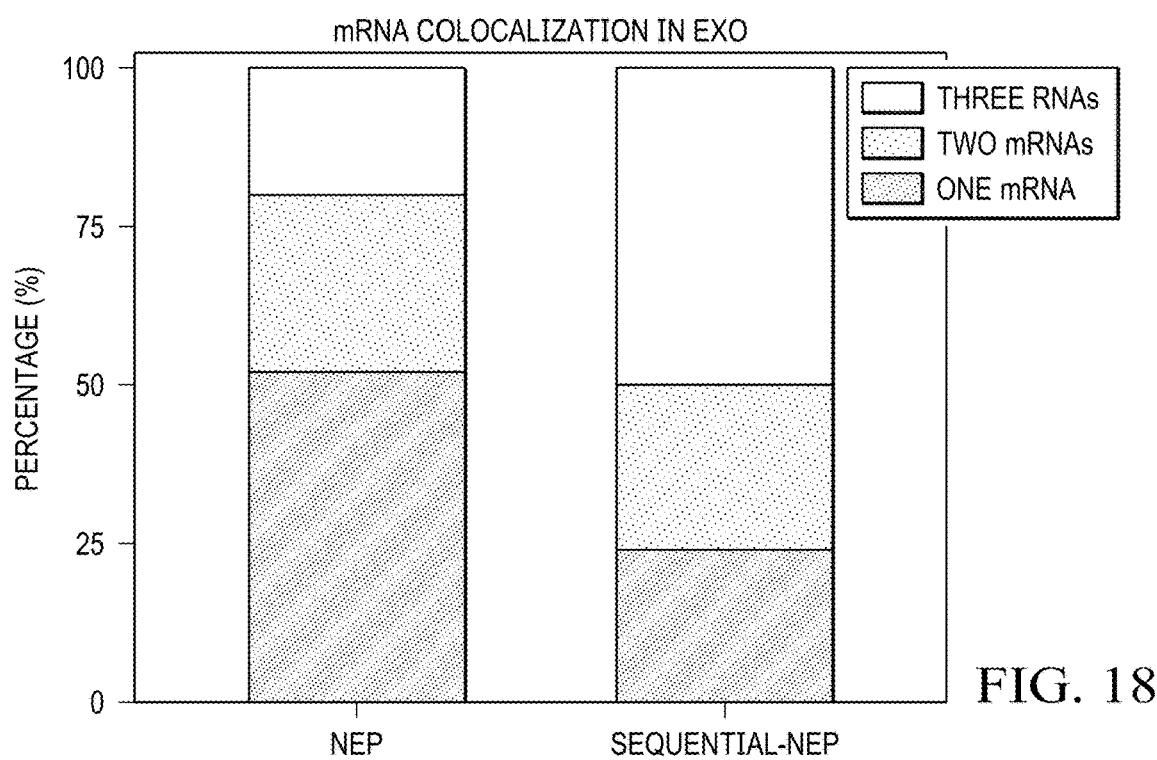

Example 4—Improvement of Multiple mRNAs Co-localized in the Same Secreted EVs by Sequential NEP Transfection of DNA Plasmids to MEF Cells FIG. 13 implies that different mRNA targets could be transcribed at different times and rates in the transfected cells, even though multiple DNA plasmids were delivered to the cells at the same time, due to the size difference of plasmids or other reasons. This may lead to individual EVs containing only one or few mRNA targets. For better therapeutic efficacy, it would be valuable if more or all mRNA targets can be encapsulated in the same secreted EVs. By sequentially delivering each DNA plasmid into MEF cells using NEP based on its transcription time, FIG. 18 shows that we could substantially increase the secreted EVs containing all three mRNAs, Ascl1, Brn2 and Myt1l (>50% vs. <25%), needed for iN reprogramming. For NEP transfection, Ascl1, Brn2 and Myt1l plasmids were transfected at the same time as described before. For sequential-NEP, the Myt1l plasmid was transfected first, Brn2 plasmid was transfected 4 h later, while Ascl1 plasmid was transfected 4 h after Brn2 transfection. At 24 h post Myt1l transfection, culture medium was collected for TLN assay. Equal amount of FAM-Ascl1, Cy3-Brn2, and Cy5-Myt1l MBs were encapsulated in tethered lipoplex nanoparticles for EV-mRNA detection. In the figure, the yellow arrow means EVs containing all 3 mRNAs, the blue arrow means EVs containing 2 mRNAs, while the pink arrow means EVs containing only 1 mRNA.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of producing extracellular vesicles (EVs), comprising:
    (a) providing an electroporation biochip, the electroporation biochip comprising: (i) a cell compartment in contact with a first surface of the electroporation biochip; (ii) a buffer compartment in contact with a second surface of the electroporation biochip; and (iii) a plurality of channels that connect the first surface of the electroporation biochip with the second surface of the electroporation biochip, wherein the plurality of channels are positioned such that individual channels of the plurality of channels contact individual donor cells within the cell compartment in contact with the first surface of the electroporation biochip;
    (b) using the electroporation biochip to sequentially deliver multiple deoxyribonucleic acid molecules (DNAs) to the donor cells, wherein the multiple DNAs are sequentially delivered based on transcription rate, thereby promoting ribonucleic acid molecules (RNAs) transcribed from the multiple DNAs to co-localize in extracellular vesicles (EVs) secreted by the donor cells; and
    (c) collecting the extracellular vesicles (EVs) secreted by the donor cells, wherein the extracellular vesicles (EVs) comprise RNAs transcribed from the multiple DNAs.

2. The method of claim 1, wherein each DNA of the multiple DNAs is a DNA plasmid, a DNA vector, or a combination thereof.

3. The method of claim 1, wherein the RNAs transcribed from the multiple DNAs comprise messenger RNAs (mRNAs), non-coding RNAs, microRNAs (miRNAs), short hairpin RNAs (shRNAs), and any combination thereof.

4. The method of claim 1, wherein a DNA of the multiple DNAs is a DNA plasmid or a DNA vector encoding CD63, CD9, or combination thereof delivered into the donor cells.

5. The method of claim 1, further comprising delivering a biomolecule or therapeutic drug to the donor cells by an additional method of transfection.

6. The method of claim 5, wherein the additional method of transfection is selected from the group consisting of gene gun, microinjection, and nanoinjection.

7. The method of claim 1, wherein the sequential delivery of the multiple DNAs to the donor cells comprises delivering each DNA of the multiple DNAs to the donor cells in a descending order according to the size of each DNA of the multiple DNAs.

8. The method of claim 1, wherein the extracellular vesicles (EVs) are collected within 4 hours following delivery of the multiple DNAs to the donor cells.

9. The method of claim 1, wherein the extracellular vesicles (EVs) are collected within 24 hours following delivery of the multiple DNAs to the donor cells.

10. The method of claim 1, wherein the extracellular vesicles (EVs) are collected within 44 hours following delivery of the multiple DNAs to the donor cells.

11. The method of claim 1, wherein the extracellular vesicles (EVs) have a median diameter larger than 47.5 nm.

12. The method of claim 1, wherein the RNAs transcribed from the multiple DNAs comprise messenger RNAs (mRNAs).

13. The method of claim 1, wherein the RNAs transcribed from the multiple DNAs comprise intact mRNAs, wherein each intact mRNA of the intact mRNAs is able to produce a protein detectable by Western Blot.

14. The method of claim 13, wherein each intact mRNA of the intact mRNAs is capable of producing the protein in vitro.

15. The method of claim 14, wherein the protein possesses a therapeutic function.

16. The method of claim 1, wherein the extracellular vesicles (EVs) comprise exosomes.

17. The method of claim 16, wherein the exosomes express Tsg101, CD9, or CD63.

18. The method of claim 16, wherein the exosomes have a diameter ranging from 40 nanometers (nm) to 110 nanometers (nm).

19. The method of claim 1, wherein the extracellular vesicles (EVs) comprise exosomes or microvesicles.

20. The method of claim 1, wherein the extracellular vesicles (EVs) comprise exosomes and microvesicles, and wherein the method further comprises separating the exosomes from the microvesicles.

21. The method of claim 20, wherein separating the exosomes from the microvesicles is performed by ultracentrifugation.

22. The method of claim 1, further comprising culturing the donor cells in a fresh medium following the delivery of the multiple DNAs to the donor cells.

23. The method of claim 1, wherein the extracellular vesicles (EVs) are collected at multiple time points.

24. The method of claim 1, wherein the extracellular vesicles (EVs) are quantified.

25. The method of claim 1, wherein the extracellular vesicles (EVs) have therapeutic functions.

* * * * *